US012698308B2

(12) United States Patent
Sohn

(10) Patent No.: US 12,698,308 B2
(45) Date of Patent: Aug. 4, 2026

(54) PEPTIDE FOR PREVENTING OR TREATING INFLAMMATORY DISEASES

(71) Applicant: AJOU UNIVERSITY INDUSTRY-ACADEMIC COOPERATION FOUNDATION, Suwon-si (KR)

(72) Inventor: Seong Hyang Sohn, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 450 days.

(21) Appl. No.: 18/554,481

(22) PCT Filed: Apr. 1, 2022

(86) PCT No.: PCT/KR2022/004715
    § 371 (c)(1),
    (2) Date: Oct. 9, 2023

(87) PCT Pub. No.: WO2022/215961
    PCT Pub. Date: Oct. 13, 2022

(65) Prior Publication Data
    US 2024/0150407 A1     May 9, 2024

(30) Foreign Application Priority Data

Apr. 9, 2021    (KR) ........................ 10-2021-0046538
    Mar. 18, 2022    (KR) ........................ 10-2022-0033914

(51) Int. Cl.
    *A23L 33/18*    (2016.01)
    *A61K 47/56*    (2017.01)
    *A61P 37/06*    (2006.01)
    *C07K 14/00*    (2006.01)

(52) U.S. Cl.
    CPC ............ *C07K 14/001* (2013.01); *A23L 33/18* (2016.08); *A61K 47/56* (2017.08); *A61P 37/06* (2018.01)

(58) Field of Classification Search
    CPC .............................. C07K 14/001; A23L 33/18
    See application file for complete search history.

(56) References Cited

U.S. PATENT DOCUMENTS

2018/0228912 A1    8/2018    Saint-Remy et al.

FOREIGN PATENT DOCUMENTS

JP        2020-511543    A    4/2020
KR    10-2012-0095063    A    8/2012
KR    10-2014-0005110    A    1/2014
KR        10-1713143    B1    3/2017
KR    10-2017-0106167    A    9/2017
KR    10-2020-0011377    A    2/2020
KR    10-2020-0101726    A    8/2020
KR    10-2021-0070911    A1    6/2021
WO        2015-087334    A1    6/2015
WO        2021/112614    A1    6/2021

*Primary Examiner* — Amber D Steele

(74) *Attorney, Agent, or Firm* — NKL LAW; Jae Youn Kim

(57) ABSTRACT

The present invention relates to: a peptide consisting of an amino acid sequence selected from the group consisting of SEQ ID NOS: 4 to 7 or a fragment thereof; and a pharmaceutical composition for the treatment or prevention of inflammatory diseases or autoimmune diseases, comprising same. The peptide has been confirmed to have an excellent effect of inhibiting cytokines such as IL-17 and TNF alpha, and thus can be provided as a therapeutic agent for various inflammatory diseases, including Behcet's disease.

13 Claims, 28 Drawing Sheets

Specification includes a Sequence Listing.

Unstained control

BD treated with P124

BD treated with P124-M

SEQUENCE LISTING

```
<160> NUMBER OF SEQ ID NOS: 7

<210> SEQ ID NO 1
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: P1

<400> SEQUENCE: 1

Leu Ile Cys Pro Glu Lys Tyr Cys Asn Lys Val His Thr
1               5                   10

<210> SEQ ID NO 2
<211> LENGTH: 11
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: P2

<400> SEQUENCE: 2

Tyr Cys Asn Lys Val His Thr Cys Arg Asn Gly
1               5                   10

<210> SEQ ID NO 3
<211> LENGTH: 11
```

-continued

```
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: P4

<400> SEQUENCE: 3

His Thr Cys Arg Asn Gly Glu Asn Ile Cys Phe
1               5                   10

<210> SEQ ID NO 4
<211> LENGTH: 22
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: E1

<400> SEQUENCE: 4

Leu Ile Cys Pro Glu Lys Tyr Cys Asn Lys Val His Thr Cys Arg Asn
1               5                   10                  15

Gly Glu Asn Ile Cys Phe
            20

<210> SEQ ID NO 5
<211> LENGTH: 25
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: E2

<400> SEQUENCE: 5

Leu Thr Cys Leu Ile Cys Pro Glu Lys Tyr Cys Asn Lys Val His Thr
1               5                   10                  15

Cys Arg Asn Gly Glu Asn Ile Cys Phe
            20                  25

<210> SEQ ID NO 6
<211> LENGTH: 21
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: E3

<400> SEQUENCE: 6

Thr Cys Pro Glu Ala Lys Pro Arg Glu Ile Val Glu Cys Cys Ser Thr
1               5                   10                  15

Asp Lys Cys Asn His
            20

<210> SEQ ID NO 7
<211> LENGTH: 25
<212> TYPE: PRT
<213> ORGANISM: Artificial Sequence
<220> FEATURE:
<223> OTHER INFORMATION: synthesized
<220> FEATURE:
<221> NAME/KEY: misc_feature
```

-continued

```
<223> OTHER INFORMATION: E4

<400> SEQUENCE: 7

Gly Cys Ala Ala Thr Cys Pro Glu Ala Lys Pro Arg Glu Ile Val Glu
1               5                   10                  15

Cys Cys Ser Thr Asp Lys Cys Asn His
            20                  25
```

PEPTIDE FOR PREVENTING OR TREATING INFLAMMATORY DISEASES

INCORPORATION OF SEQUENCE LISTING

This application contains a sequence listing submitted in Computer Readable Form (CRF). The CFR file containing the sequence listing entitled "10-PK6676431-SequenceListing.txt", which was created on Oct. 9, 2023, and is 2,532 bytes in size. The information in the sequence listing is incorporated herein by reference in its entirety.

TECHNICAL FIELD

The present disclosure provides a peptide for preventing or treating inflammatory diseases, and more specifically, a composition for preventing or treating inflammatory diseases or autoimmune diseases including a peptide having an amino acid sequence selected from the group consisting of SEQ ID NOS: 4 to 7 or a fragment thereof.

BACKGROUND ART

Inflammation or immune response is a very important biological phenomenon to protect our body from foreign substances such as bacteria and viruses using various inflammatory cells and immune cells. For example, the immune system induces secretion of anti-inflammatory cytokines to enhance the immune response, thereby protecting our body from attacks by foreign pathogens.

However, when an innately excessive inflammatory or immune response is induced due to a variety of causes including genetic and environmental factors, a variety of pathological conditions may occur. Once the immune response to protect our body from foreign substances is activated, if this response is not properly alleviated, an excessive immune response may be kept on continuously, which may eventually lead to autoimmune diseases to attack the normal components that make up the body.

Behçet's disease, one of the inflammatory diseases or autoimmune diseases, is a rare and intractable inflammatory disease characterized by recurrent aphthous ulcers, uveitis, skin inflammation, and ulcer in the mouth and/or genitals. Clinical symptoms are multifaceted, including not only skin ulcers, but also severe chronic inflammation accompanied by symptoms in joints, central nervous system, gastrointestinal, renal, genitourinary, pulmonary, cardiovascular systems, digestive systems such as intestinal hemorrhage and intestinal perforation, superior and inferior vena cava syndrome, and aortic regurgitation. These symptoms are associated with systemic vasculitis and are the major pathophysiological feature of Behçet's disease. The exact onset cause of Behçet's disease remains unclear, but autoimmune and autoinflammatory responses are important causes.

Cytokines such as interleukin-17 and TNF alpha are expressed in a high level in the plasma of patients with Behcet's disease, causing inflammatory symptoms. Though new biodrugs such as TNF alpha antibody are currently used as a therapeutic agent for Behçet's disease, the cost is very high with reported side effects such as tuberculosis bacillus infection, and there is a tendency in that repeated use reduces the therapeutic effect due to resistance.

Therefore, there is still a need to develop new therapeutic agents that may reduce side effects while securing cost-competitiveness, in an attempt to efficiently treat inflammatory diseases or autoimmune diseases, including Behçet's disease.

DISCLOSURE OF THE INVENTION

Technical Goals

An object of the present disclosure is to provide a peptide having an amino acid sequence selected from the group consisting of SEQ ID NOS: 4 to 7 or a fragment thereof.

Another object of the present disclosure is to provide a conjugate in which the peptide or a fragment thereof is conjugated to a biocompatible polymer or fatty acid.

Another object of the present disclosure is to provide a pharmaceutical composition for treating or preventing inflammatory diseases or autoimmune diseases, including one or two or more selected from the group consisting of the peptide or a fragment thereof; and the conjugate as an active ingredient.

Another object of the present disclosure is to provide a cosmetic composition for preventing or alleviating inflammatory diseases or autoimmune diseases, including one or two or more selected from the group consisting of the peptide or a fragment thereof; and the conjugate as an active ingredient.

Another object of the present disclosure is to provide a health functional food composition for preventing or alleviating inflammatory diseases or autoimmune diseases, including one or two or more selected from the group consisting of the peptide or a fragment thereof; and the conjugate as an active ingredient.

Technical Solutions

To achieve the above object, the present disclosure provides a peptide having an amino acid sequence selected from the group consisting of SEQ ID NOS: 4 to 7 or a fragment thereof.

In addition, the present disclosure provides a conjugate in which the peptide or a fragment thereof is conjugated to a biocompatible polymer or fatty acid.

In addition, the present disclosure provides a pharmaceutical composition for treating or preventing inflammatory diseases or autoimmune diseases, including one or two or more selected from the group consisting of the peptide or a fragment thereof; and the conjugate as an active ingredient.

In addition, the present disclosure provides a cosmetic composition for preventing or alleviating inflammatory diseases or autoimmune diseases, including one or two or more selected from the group consisting of the peptide or a fragment thereof; and the conjugate as an active ingredient.

In addition, the present disclosure provides a health functional food composition for preventing or alleviating inflammatory diseases or autoimmune diseases, including one or two or more selected from the group consisting of the peptide or a fragment thereof; and the conjugate as an active ingredient.

Advantageous Effects

The present disclosure relates to a technology to provide a peptide having an amino acid sequence selected from the group consisting of SEQ ID NOS: 4 to 7 or a fragment thereof and a medical use thereof, wherein the peptide may be modified as an end is lipidized and has an excellent effect of inhibiting cytokines such as IL-17 and TNF alpha, such that the peptide may be used as a therapeutic agent for various inflammatory diseases or autoimmune diseases, including Behçet's disease or arthritis.

BEST MODE FOR CARRYING OUT THE INVENTION

Figure 1A:
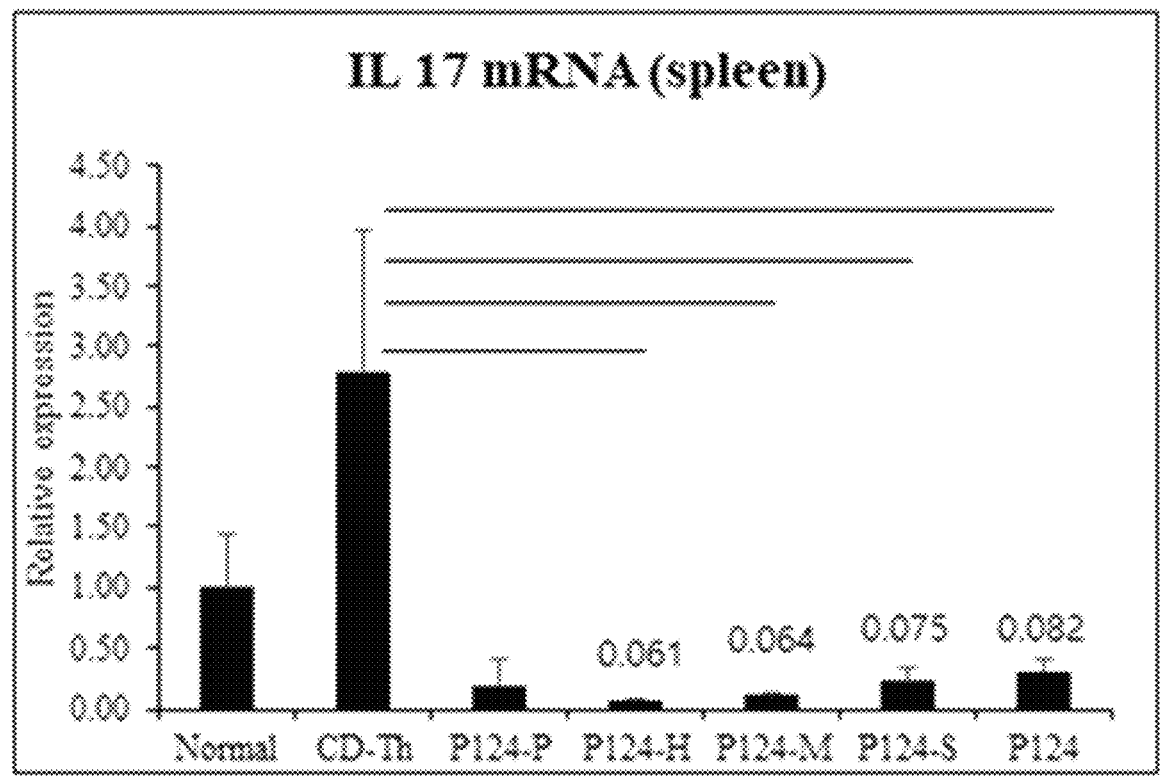
FIGS. 1A-1B show results of genetic analysis via real-time PCR by injecting IL-6, TGF beta, and IL-23 into the abdominal cavity of mice to induce Th17 cells (CD-Th), intraperitoneally administering each peptide, and isolating splenocytes after 24 hours.

Hereinafter, the present disclosure will be described in more detail.

Conventionally, biodrugs such as TNF alpha antibodies are used as therapeutic agents for Behçet's disease or arthritis, but the cost is very high with reported side effects such as tuberculosis bacillus infection, such that, in order to overcome the shortcomings, the present disclosure was completed, which has amino acid sequences selected from the group consisting of SEQ ID NO: 4 to 7.

The present disclosure provides a peptide having an amino acid sequence selected from the group consisting of SEQ ID NOS: 4 to 7 or a fragment thereof.

The fragment may be an amino acid sequence selected from the group consisting of SEQ ID NOS: 1 to 3.

N or C terminus of the peptide or fragment thereof may be subjected to palmitoylation, hexanoylation, myristoylation, stearoylation, acetylation, maleimidobutyroylation, or PEGylation, but is not limited thereto.

The peptide or fragment thereof may penetrate a skin tissue and pass through a cell membrane.

The peptide or fragment thereof may have an immunomodulatory function or anti-inflammatory activity.

The peptide or fragment thereof may inhibit an activity of IL-17, TNF-alpha, or IL-1 beta cytokines.

In addition, the present disclosure provides a conjugate in which the peptide or fragment thereof is conjugated to a biocompatible polymer or fatty acid.

The biocompatible polymer may be one or two or more selected from the group consisting of pullulan, chondroitin sulfate, hyaluronic acid (HA), glycol chitosan, starch, chitosan, dextran, pectin, curdlan, poly-L-lysine, poly-aspartic acid (PAA), polylactic acid (PLA), polyglycolide (PGA), poly(ε-caprolactone) (PCL), poly(caprolactone-lactide) random copolymer (PCLA), poly(caprolactone-glycolide) random copolymer (PCGA), poly(lactide-glycolide) random copolymer (PCGA), polyethylene glycol (PEG), pluronic F-68, and pluronic F-127, but is not limited thereto.

The fatty acid may be one or two or more selected from the group consisting of hexanoic acid, caprylic acid, capric acid, maleimidobutyric acid, lauric acid, myristic acid, palmitic acid, stearic acid, and cholesterol, but is not limited thereto.

In addition, the present disclosure provides a pharmaceutical composition for treating or preventing inflammatory diseases or autoimmune diseases, including one or two or more selected from the group consisting of the peptide or a fragment thereof; and the conjugate according to as an active ingredient.

The inflammatory disease or autoimmune disease may be selected from the group consisting of Behçet's disease, osteoarthritis, rheumatoid arthritis, dermatitis, allergies, atopy, asthma, psoriasis, conjunctivitis, rhinitis, otitis media, sore throat, tonsillitis, pneumonia, ulcer, gastritis, Crohn's disease, inflammatory bowel disease, lupus, hepatitis, cystitis, interstitial cystitis, nephritis, Sjogren's syndrome, multiple sclerosis, Hashimoto thyroiditis, polymyositis, scleroderma, Addison disease, vitiligo, pernicious anemia, cystic fibrosis, graft-versus-host disease, transplant rejection, autoimmune diabetes, diabetic retinopathy, ischemia-reperfusion injury, post-angioplasty restenosis, chronic obstructive pulmonary disease (COPD), Graves disease, and acute or chronic inflammatory diseases, but is not limited thereto.

In another example embodiment of the present disclosure, the pharmaceutical composition may further include one or more appropriate additives selected from the group consisting of carriers, excipients, disintegrants, sweeteners, coating agents, swelling agents, antifrictions, lubricants, flavoring agents, antioxidants, buffers, bacteriostatic agents, diluents, dispersants, surfactants, binders, and antifrictions that are commonly used in the preparation of pharmaceutical compositions.

Specifically, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil may be used as carriers, excipients, and diluents, and solid preparations for oral administration include tablets, pills, powder, granules, and capsules, wherein such solid preparation may be prepared by mixing, in the composition, at least one excipient such as starch, calcium carbonate, sucrose or lactose, and gelatin. In addition to simple excipients, lubricants such as magnesium stearate and talc may also be used. Liquid preparations for oral use may include suspensions, solutions, emulsions, and syrups, and various excipients such as wetting agents, sweeteners, fragrances, and preservatives may be included in addition to commonly used simple diluents such as water and liquid paraffin. Preparations for parenteral administration include sterile aqueous solutions, non-aqueous solutions, suspensions, emulsions, freeze-dried preparations, and suppositories. Propylene glycol, polyethylene glycol, vegetable oils such as olive oil, and injectable esters such as ethyl oleate may be used as non-aqueous solvents and suspending agents. Witepsol, macrogol, Tween 61, cacao butter, laurin fat, and glycerogelatin may be used as a base of the suppositories.

According to an example embodiment of the present disclosure, the pharmaceutical composition may be administered to a subject in a conventional manner via intravenous, intraarterial, intraperitoneal, intramuscular, intrasternal, transdermal, intranasal, inhalational, topical, rectal, oral, intraocular, or intradermal routes.

The dosage of the active ingredient according to the present disclosure may vary depending on the condition and weight of a subject, the type and severity of disease, the drug form, the route of administration and duration and be appropriately selected by those skilled in the art, and the daily dosage may be 0.01 mg/kg to 200 mg/kg, preferably 0.1 mg/kg to 200 mg/kg, more preferably 0.1 mg/kg to 100 mg/kg. Administration may be conducted once a day or in several divided doses, but the scope of the present disclosure is not limited thereby.

In addition, the present disclosure provides a cosmetic composition for preventing or alleviating inflammatory diseases or autoimmune diseases, including one or two or more selected from the group consisting of the peptide or a fragment thereof; and the conjugate as an active ingredient.

The cosmetic composition of the present disclosure is not particularly limited in its formulation, for example, it may be formulated into cosmetic products such as softening toner, astringent toner, nourishing toner, nourishing cream, massage cream, essence, eye cream, eye essence, cleansing cream, cleansing foam, cleansing water, pack, powder, body lotion, body cream, body oil, and body essence, or applied in a form to be applied to the skin or absorbed into the skin using a microneedle.

In the cosmetic composition of the present disclosure, the carriers allowed in pharmaceutical or cosmetic conventions may vary depending on the formulation thereof, but include hydrocarbons such as Vaseline, fluid paraffin, and gelated hydrocarbons (also called plastibase); animal and vegetable oils such as medium-chain fatty acid, triglycerides, pork fat, hard fat, and cacao fat; high grade alcohols such as cetanol, stearyl alcohol, stearic acid, and isopropyl palmitate as well as fatty acids and esters thereof; water-soluble bases such as macrogol(polyethylene glycol), 1,3-butylene glycol, glycerol, gelatin, white sugar, and sugar alcohol; emulsifiers such as glycerin fatty acid esters, polyoxyl stearate, and polyoxyethylene-hydrogenated castor oil; adhesives such as acrylic acid esters and sodium alginate; propellants such as liquefied petroleum gas and carbon dioxide; and preservatives such as paraoxybenzoate esters, and external agents of the present disclosure may be prepared according to a conventional method using the same. In addition to the above ingredients, stabilizers, flavoring agents, colorants, pH adjusters, diluents, surfactants, preservatives, and antioxidants may be combined as needed. The external agent of the present disclosure may be applied to the topical wound by conventional methods.

In addition, the present disclosure provides a health functional food composition for preventing or alleviating inflammatory diseases or autoimmune diseases, including one or two or more selected from the group consisting of the peptide or a fragment thereof; and the conjugate as an active ingredient.

The health functional food may include various nutritional supplements, vitamins, minerals (electrolytes), flavoring agents such as synthetic flavors and natural flavors, colorants and thickening agents (cheese, chocolate), pectic acid and salts thereof, alginic acid and salts thereof, organic acids, protective colloidal thickeners, pH regulators, stabilizers, preservatives, glycerin, alcohol, and carbonating agents used in carbonated beverages.

It may also include pulp for the manufacture of natural fruit juices, synthetic fruit juices, and vegetable beverages. These components may be used independently or in combination. In addition, the health functional food composition may be in any one form of meat, sausage, bread, chocolate, candy, snacks, confectionery, pizza, ramen, chewing gum, ice cream, soup, beverage, tea, functional water, drink, alcohol, and vitamin complex.

In addition, the health functional food may further include food additives, and the suitability as the "food additive" is determined by the standards and criteria related to corresponding items according to the general rules and general test methods of Korean Food Additives Codex approved by the Ministry of Food and Drug Safety, unless otherwise stipulated.

The items listed in the "Korean Food Additives Codex" may include, for example, chemically synthesized compounds such as ketones, glycine, potassium citrate, nicotinic acid, and cinnamic acid, natural additives such as persimmon color, licorice extracts, crystallized cellulose, kaoliang color, and guar gum, and mixed preparations such as sodium L-glutamate preparations, noodle-added alkali agents, preservative agents, and tar color agents.

In this case, the content of the active ingredient added to the food in the process of manufacturing the health functional food may be appropriately adjusted as needed, and preferably 1 to 90 parts by weight may be added to be included in 100 parts by weight of food.

MODES FOR CARRYING OUT THE INVENTION

Hereinafter, example embodiments will be described in detail to help the understanding of the present disclosure. However, the following example embodiments are merely illustrative of the content of the present disclosure, and the scope of the present disclosure is not limited to the following example embodiments. The example embodiments of the present disclosure are provided to more completely explain the present disclosure to those of ordinary skill in the art.

[Preparation Example] Types of Peptides

According to Table 1, various types of lipidation conjugation were performed on terminus of a peptide consisting of amino acid sequences of SEQ ID NOS: 1 to 7, and lipidized peptides were prepared by requesting Peptron, Inc. and Anygen Co., Ltd. N or C terminus of each modified peptide was subjected to palmitoylation (P), hexanoylation (H), myristoylation (M), stearoylation (S), acetylation (A), and maleimidobutyroylation (MA).

TABLE 1

| Peptide name | Peptide sequence | Peptide terminal modification |
|---|---|---|
| P1 | LICPEKYCNKVHT (SEQ ID NO: 1) | |
| P2 | YCNKVHTCRNG (SEQ ID NO: 2) | |
| P4 | HTCRNGENICF (SEQ ID NO: 3) | |

TABLE 1-continued

| Peptide name | Peptide sequence | Peptide terminal modification |
|---|---|---|
| P124-P | P1-P, P2-P, P4-P mixture | N terminal Palmitoylation |
| P124-H | P1-H, P2-H, P4-H mixture | N terminal Hexanoylation |
| P124-M | P1-M, P2-M, P4-M mixture | N terminal Myristoylation |
| P124-S | P1-S, P2-S, P4-S mixture | N terminal Stearoylation |
| E1 | LICPEKYCNKVHTCRNGENICF (SEQ ID NO: 4) | |
| E2 | LTCLICPEKYCNKVHTCRNGENICF (SEQ ID NO: 5) | |
| E3 | TCPEAKPREIVECCSTDKCNH (SEQ ID NO: 6) | |
| E4 | GCAATCPEAKPREIVECCSTDKCNH (SEQ ID NO: 7) | |
| E1M | | N terminal Myristoylation |
| ME1 | | C terminal Myristoylation |
| E2M | | N terminal Myristoylation |
| E3M | | N terminal Myristoylation |
| E3-Ac | | N terminal Acetylation |
| E3-H | | N terminal Hexanoylation |
| E3-My | | N terminal Myristoylation |
| E3-P | | N terminal Palmitoylation |
| E3-S | | N terminal Stearoylation |
| E4-Ac | | N terminal Acetylation |
| E4-H | | N terminal Hexanoylation |
| E4-My | | N terminal Myristoylation |
| E4-P | | N terminal Palmitoylation |
| E4-S | | N terminal Stearoylation |
| E4-MA | | N terminal Maleimidobutyroylation |

[Experimental Example 1] Genetic Analysis Via Real-Time PCR In Vivo 4-week-old male ICR mice (purchased from ORIENT BIO Inc.) weighing 25 g were subjected to intraperitoneal injection with 200 µL of a solution including 2 µg of anti-CD3 Ab, 2 µg of anti-CD28 Ab, 40 ng of IL-6, 10 ng of TGF beta, and 40 ng of IL-23, Th17 cells were induced (CD-Th) after 24 hours, each peptide was dissolved in 200 µL of distilled water by 0.1 µg each and administered intraperitoneally, and after 24 hours, splenocytes were isolated to analyze genes by real-time PCR.

Figure 1B:
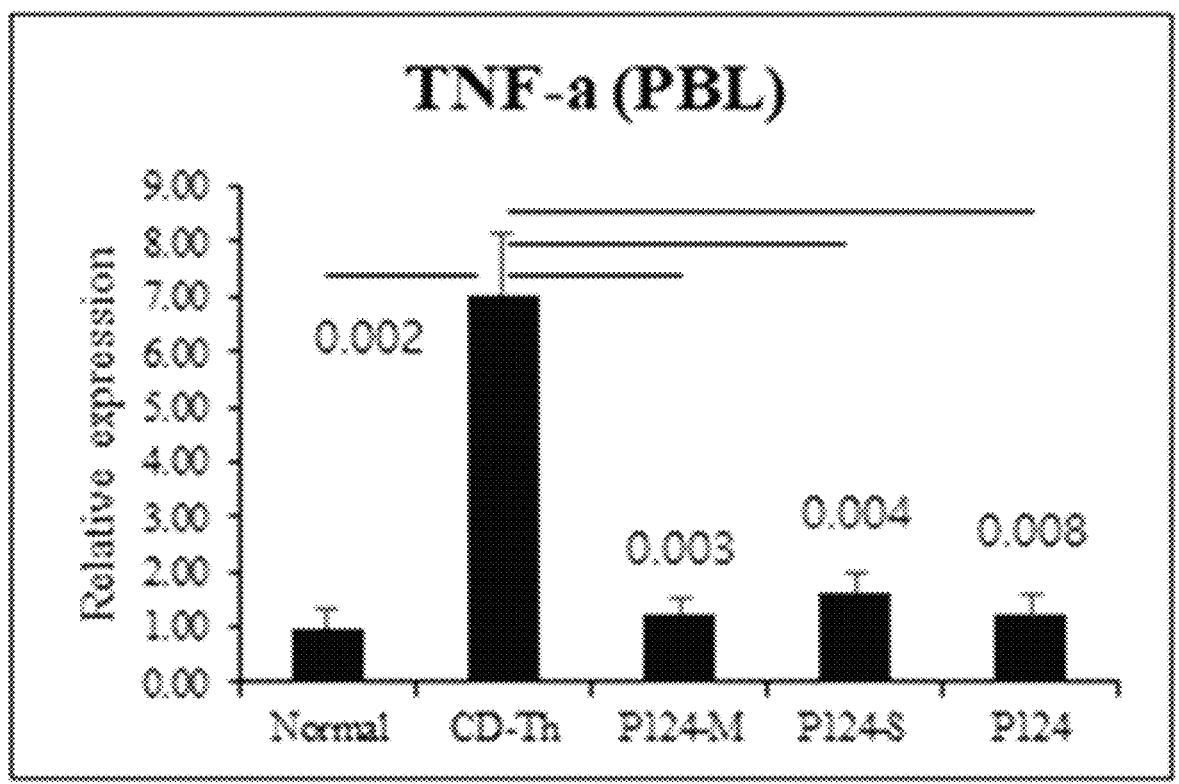

As a result, according to FIGS. 1A-1B, when lipidized to the peptides (P124-P, P124-H, P124-M, and P124-S), the IL-17 inhibitory function was enhanced compared to the unconjugated peptide (P124), and the TNF-alpha inhibitory function was enhanced in P124-M and P124-S peptides compared to P124.

[Experimental Example 2] Genetic Analysis Via Real-Time PCR In Vitro

While culturing spleen cells isolated from the spleen of 4-week-old male ICR mice weighing 25 g, various types of peptides having lipidized at terminus of the peptides were treated to cells, and changes in cytokine expression were observed via real-time PCR. Spleen cell isolation was performed by cutting out the spleen from mice, placing the spleen on a cell filter, crushing the spleen on a Petri dish through the cell filter using the plunger tip of a syringe, rinsing the cell filter with PBS, and transferring the suspended cells to 15 mL conical tube. Cells were centrifuged at 4° C. and 800×g for 5 minutes. Subsequently, the supernatant was discarded, and the pellets were resuspended in 1 mL of ACK buffer (ammonium-chloride-potassium lysing buffer). After leaving at room temperature for 5 to 10 minutes, 40 mL of PBS at 4° C. was added, and the cells were centrifuged again at 4° C. and 800×g for 5 minutes. The supernatant was discarded again, the pellets were resuspended in 5 mL of culture, and $2 \times 10^6$ cells/mL were cultured in DMEM medium. Before culturing spleen cells in an incubator, 1 µg/mL anti-CD3 Ab was coated on the bottom of a culture container, after 24 hours, culture was performed for 3 days in DMEM medium including 1 µg of anti-CD28 Ab, 20 ng of IL-6, 5 ng of TGF beta, and 20 ng of IL-23 per 1 mL of culture medium, and then the peptides were treated, followed by culture for another 24 hours.

Figure 2A:
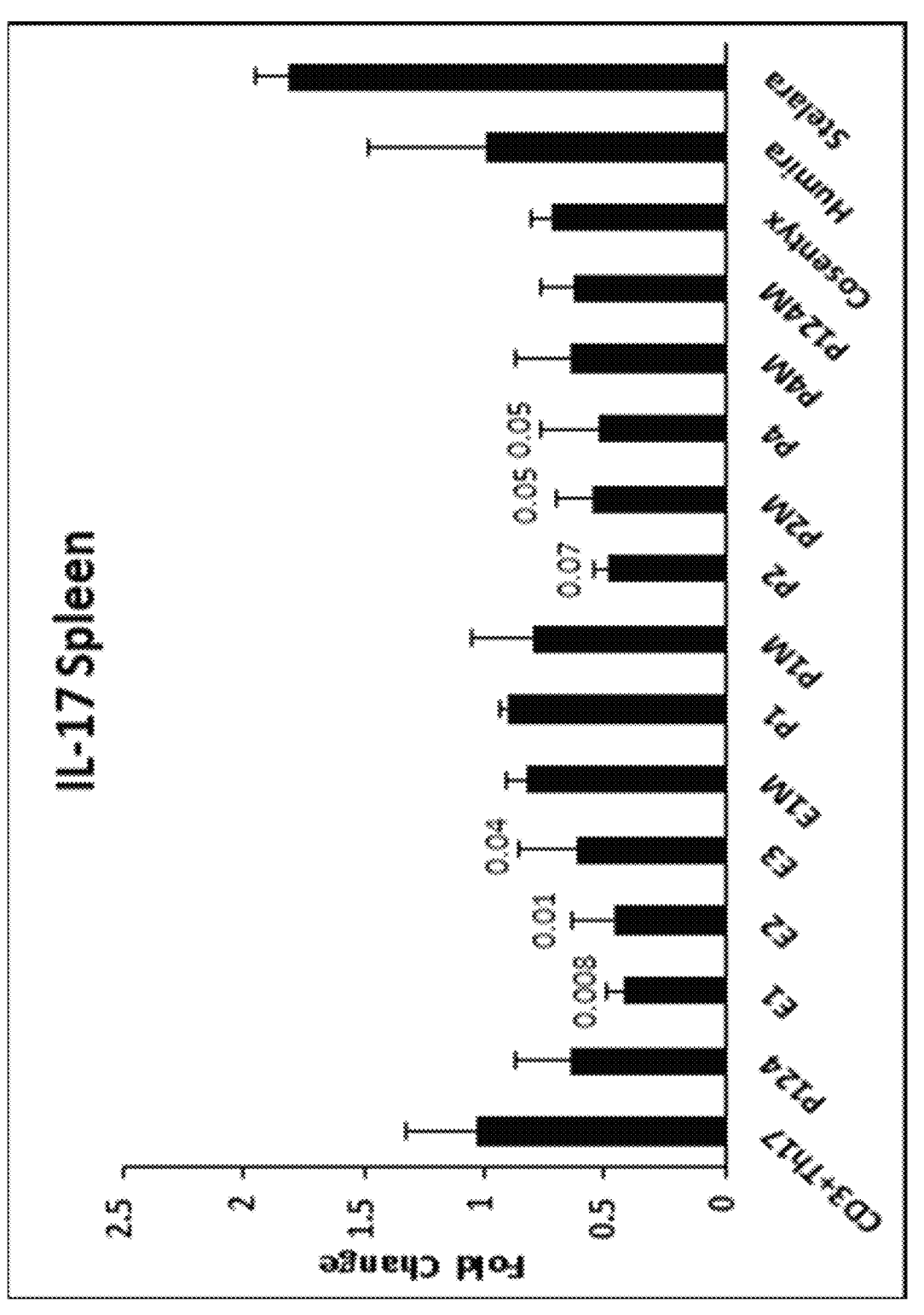
FIGS. 2A-2I show changes in cytokine expression via real-time PCR after administering, into mice, various types of peptides having lipidized terminals on the peptides.
Figure 2B:
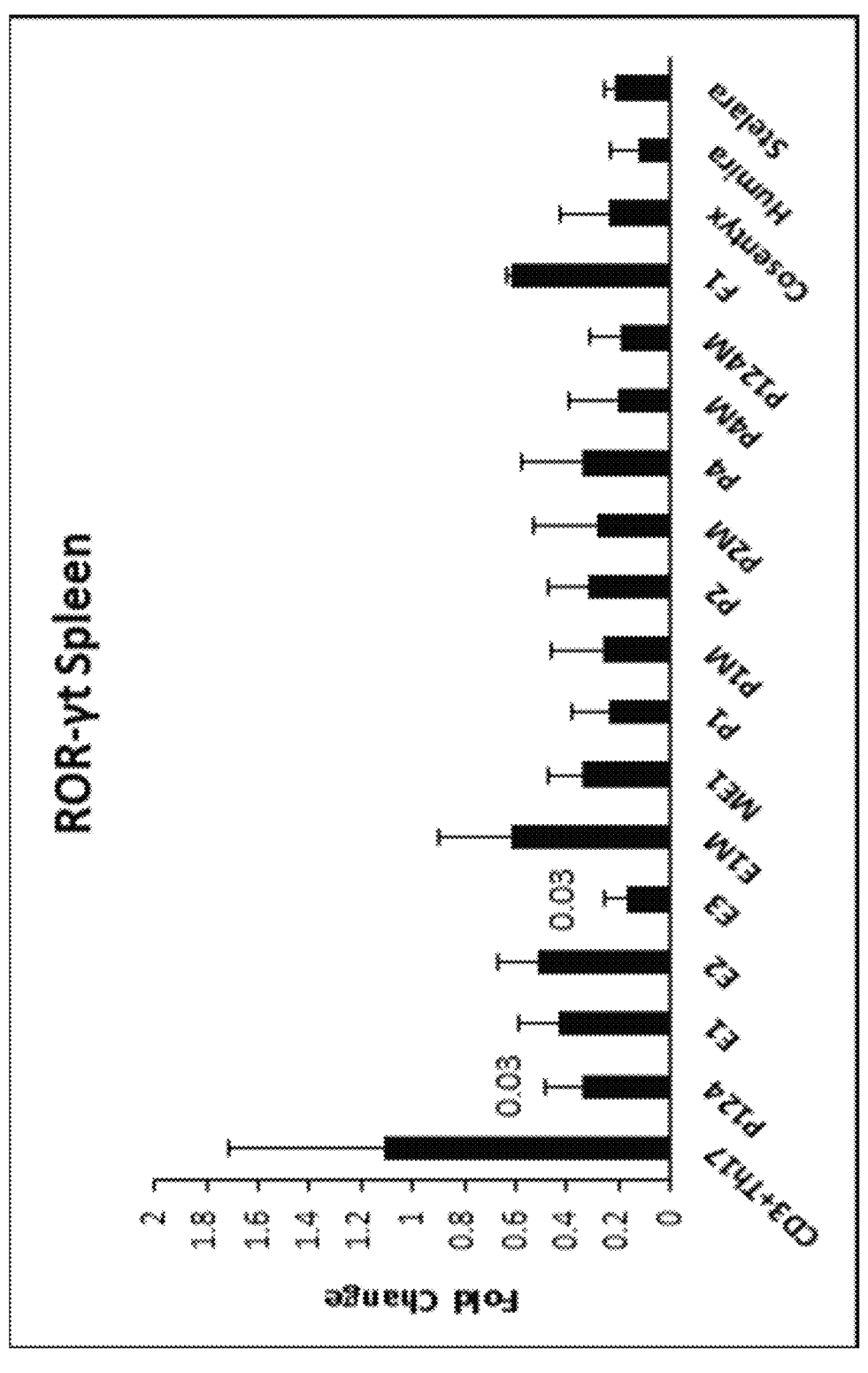
Figure 2C:
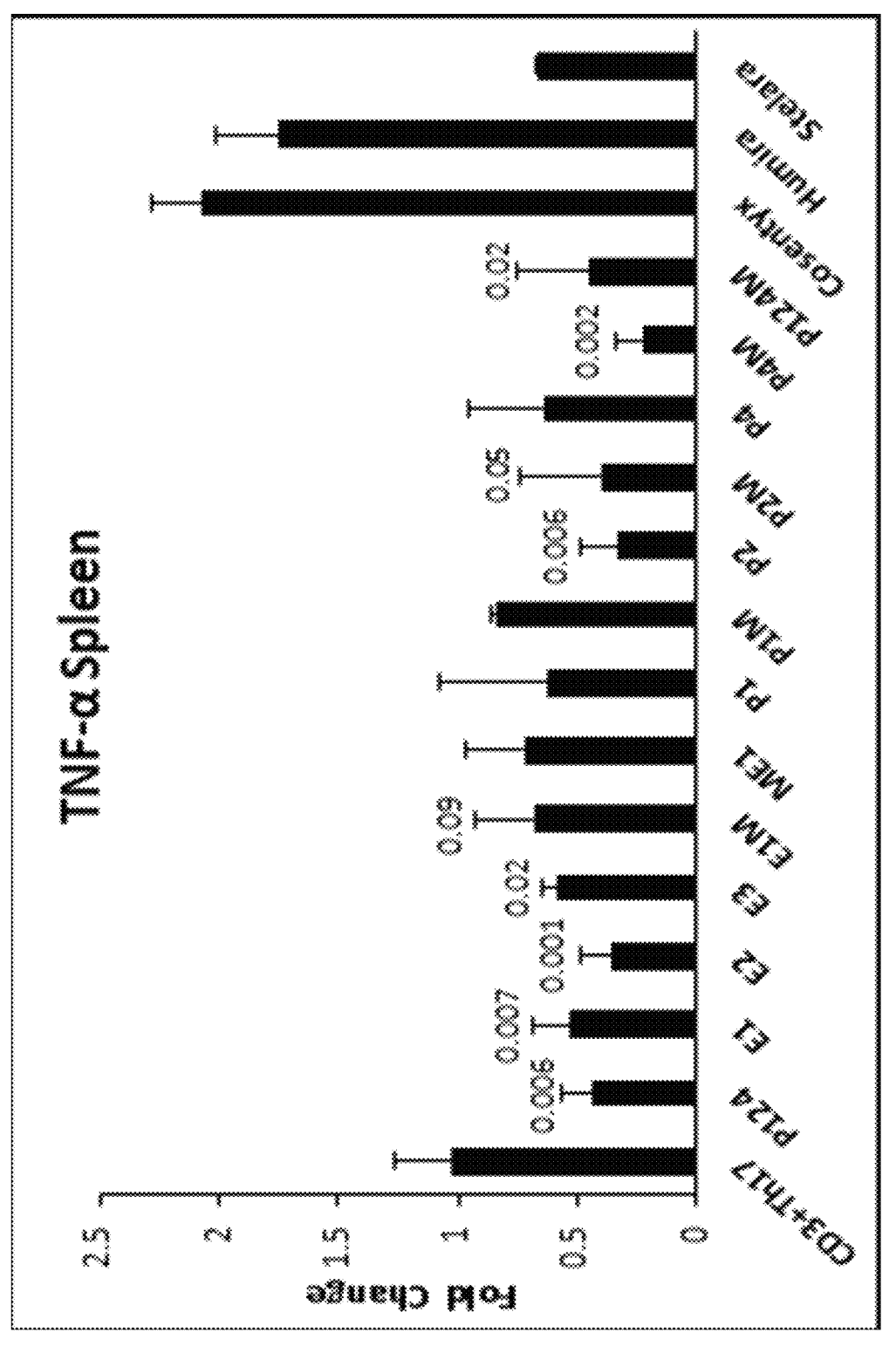
Figure 2D:
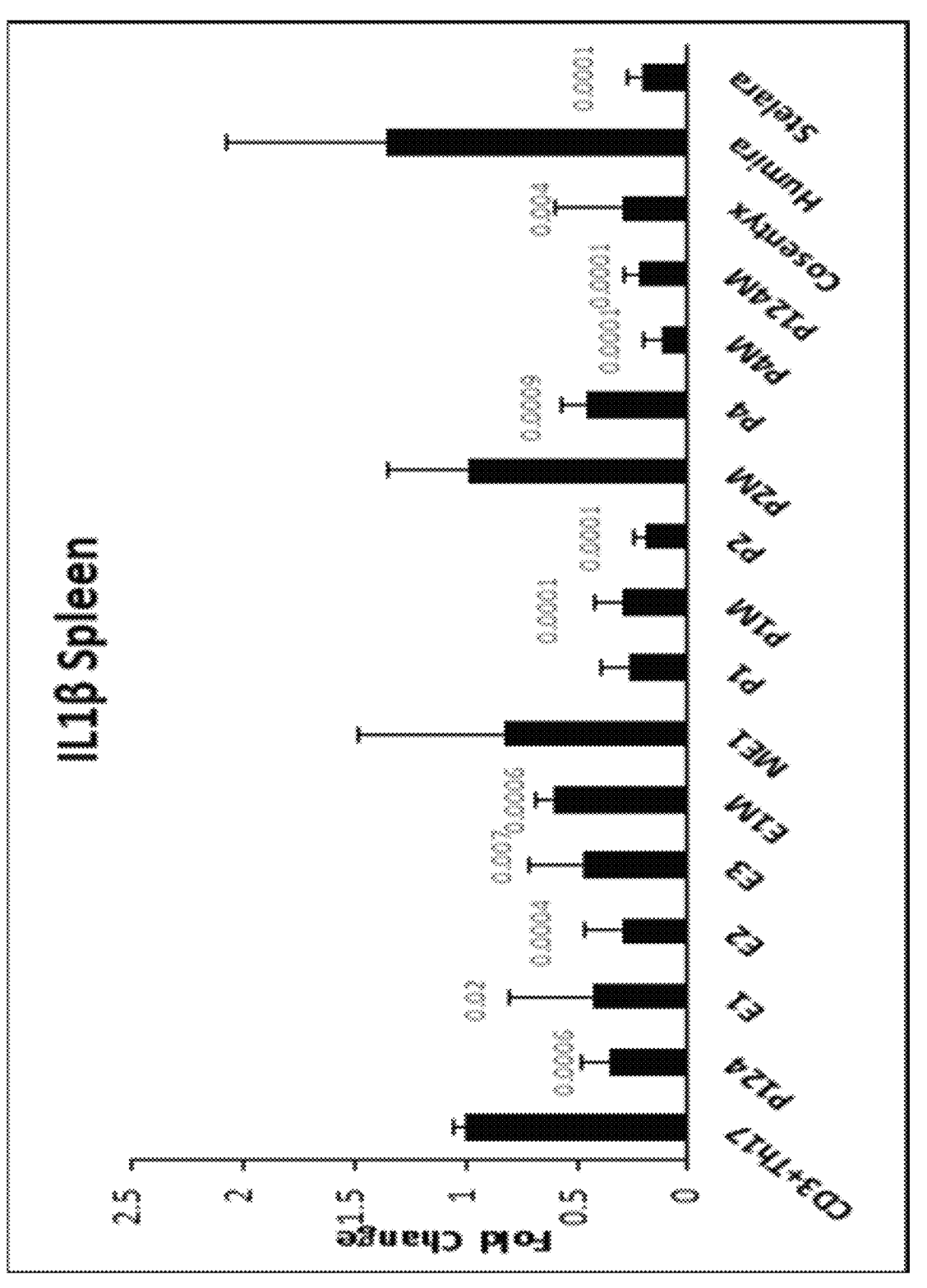
Figure 2E:
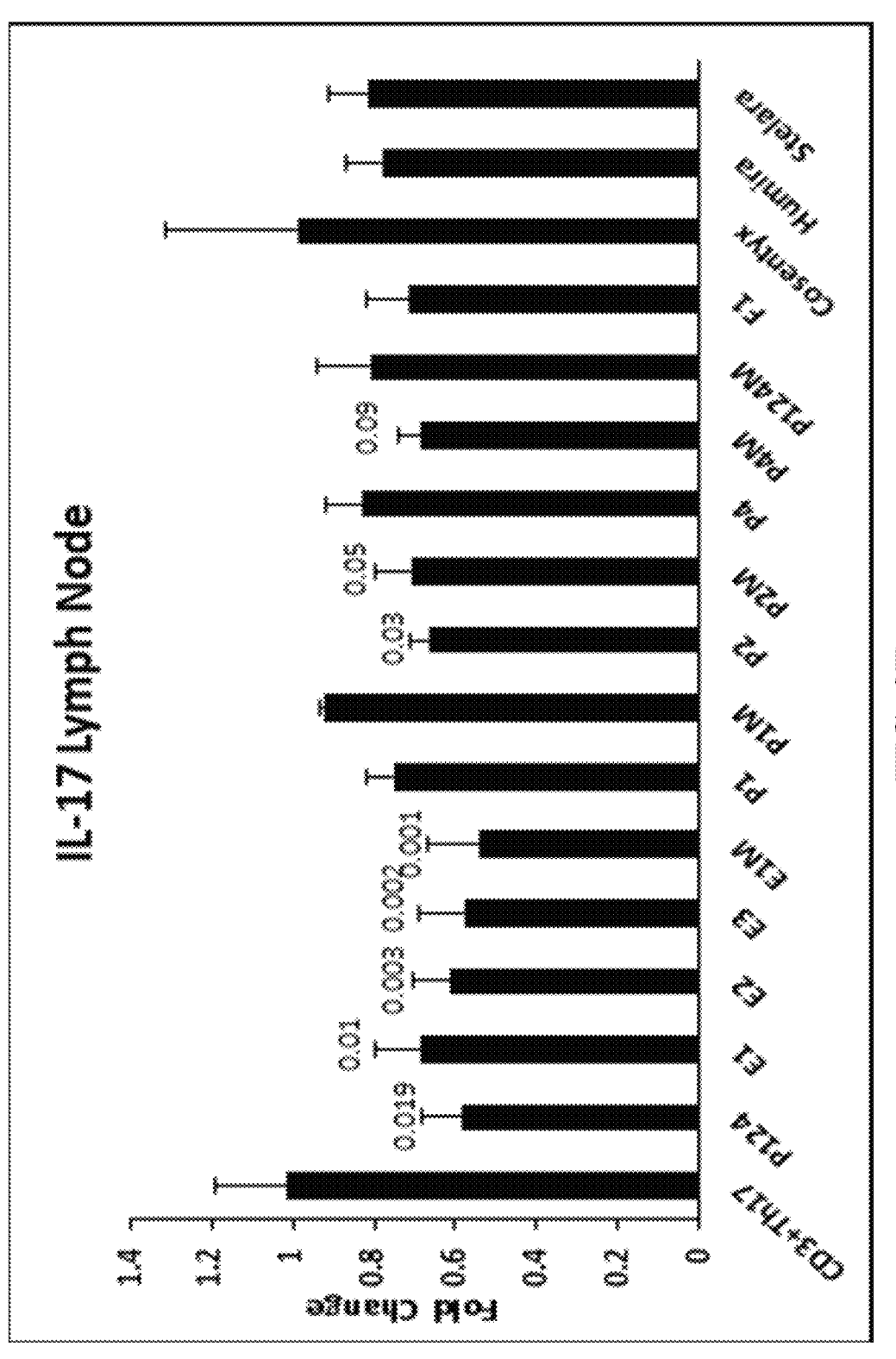
Figure 2F:
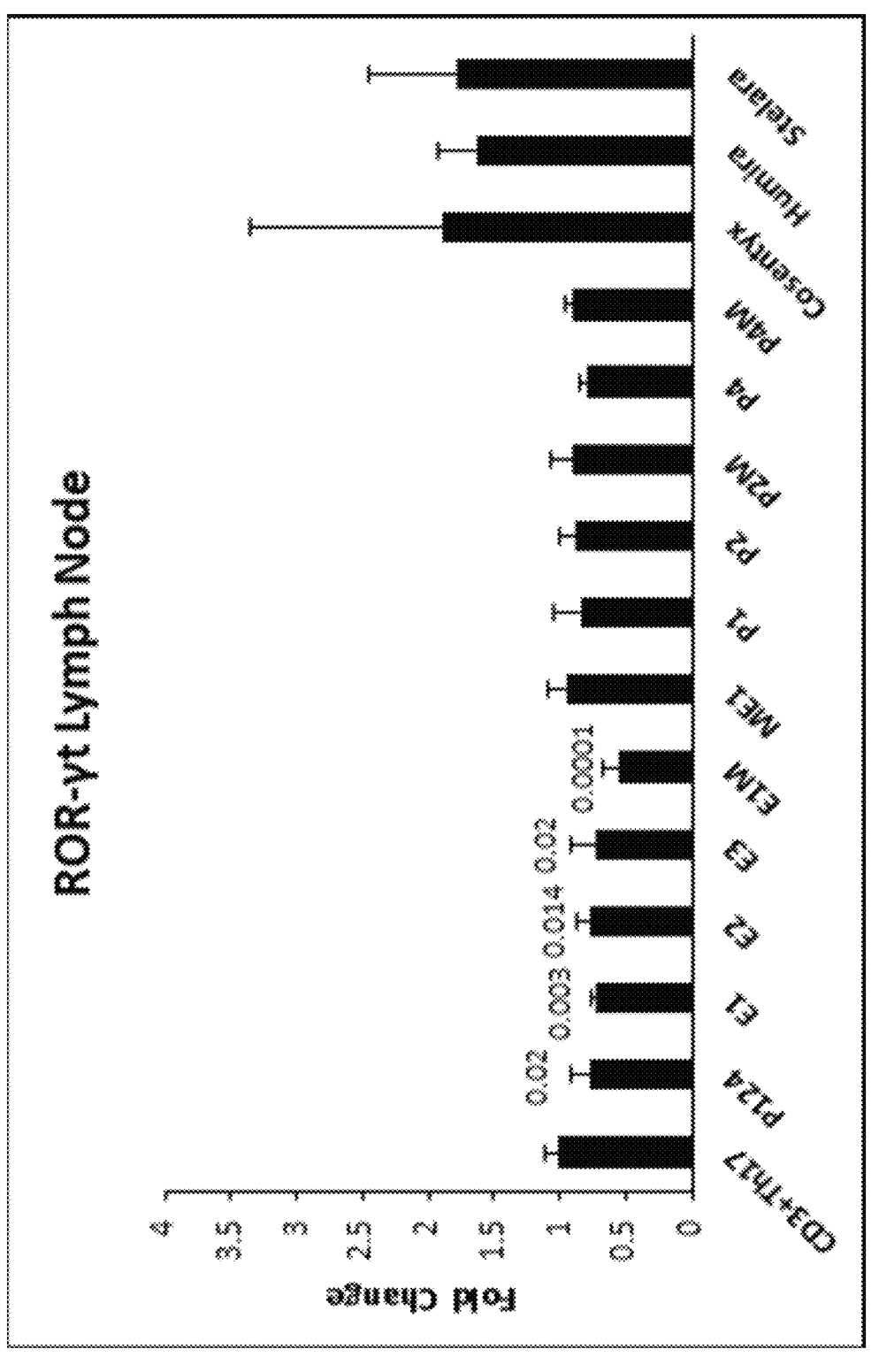
Figure 2G:
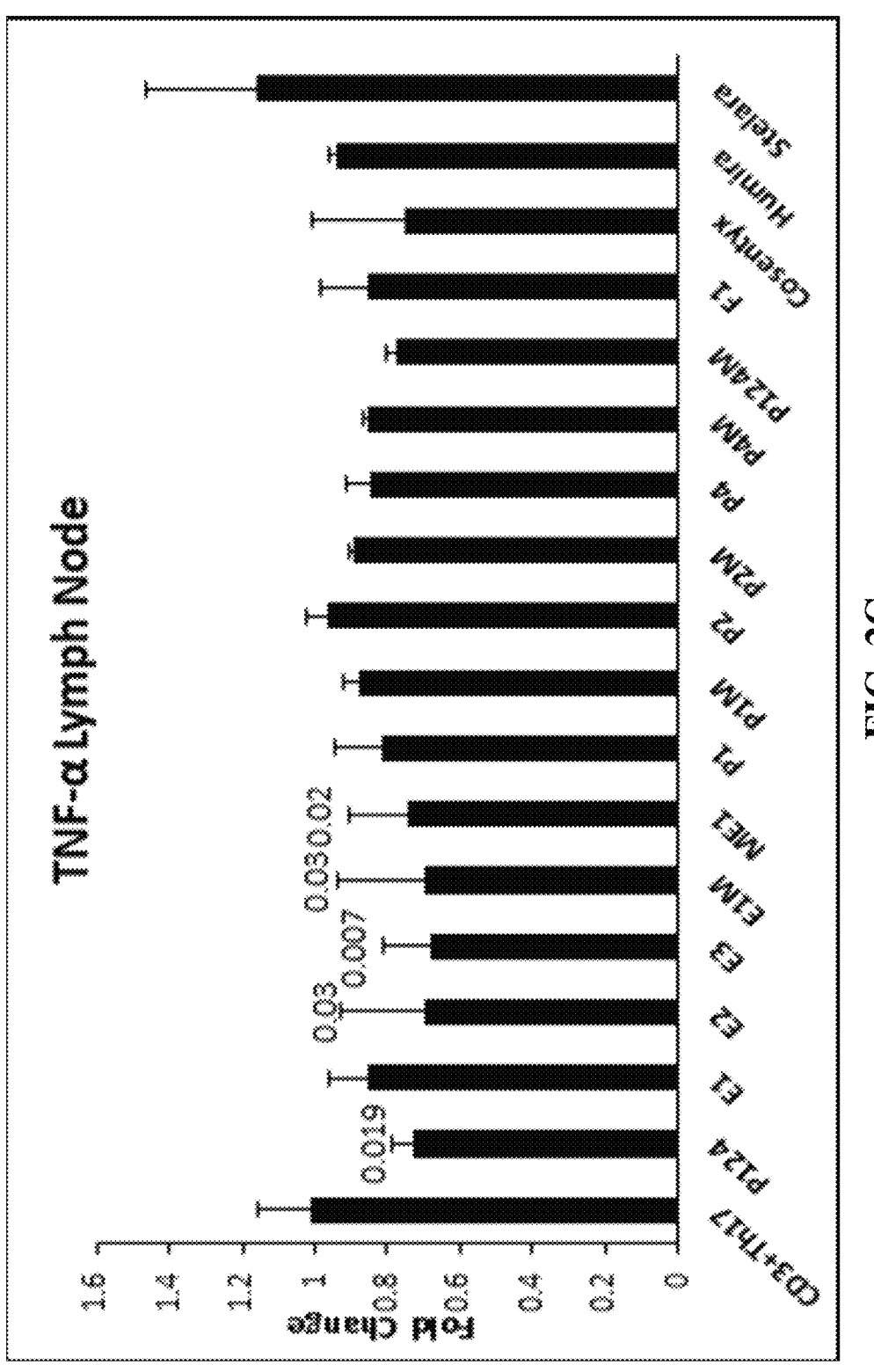
Figure 2H:
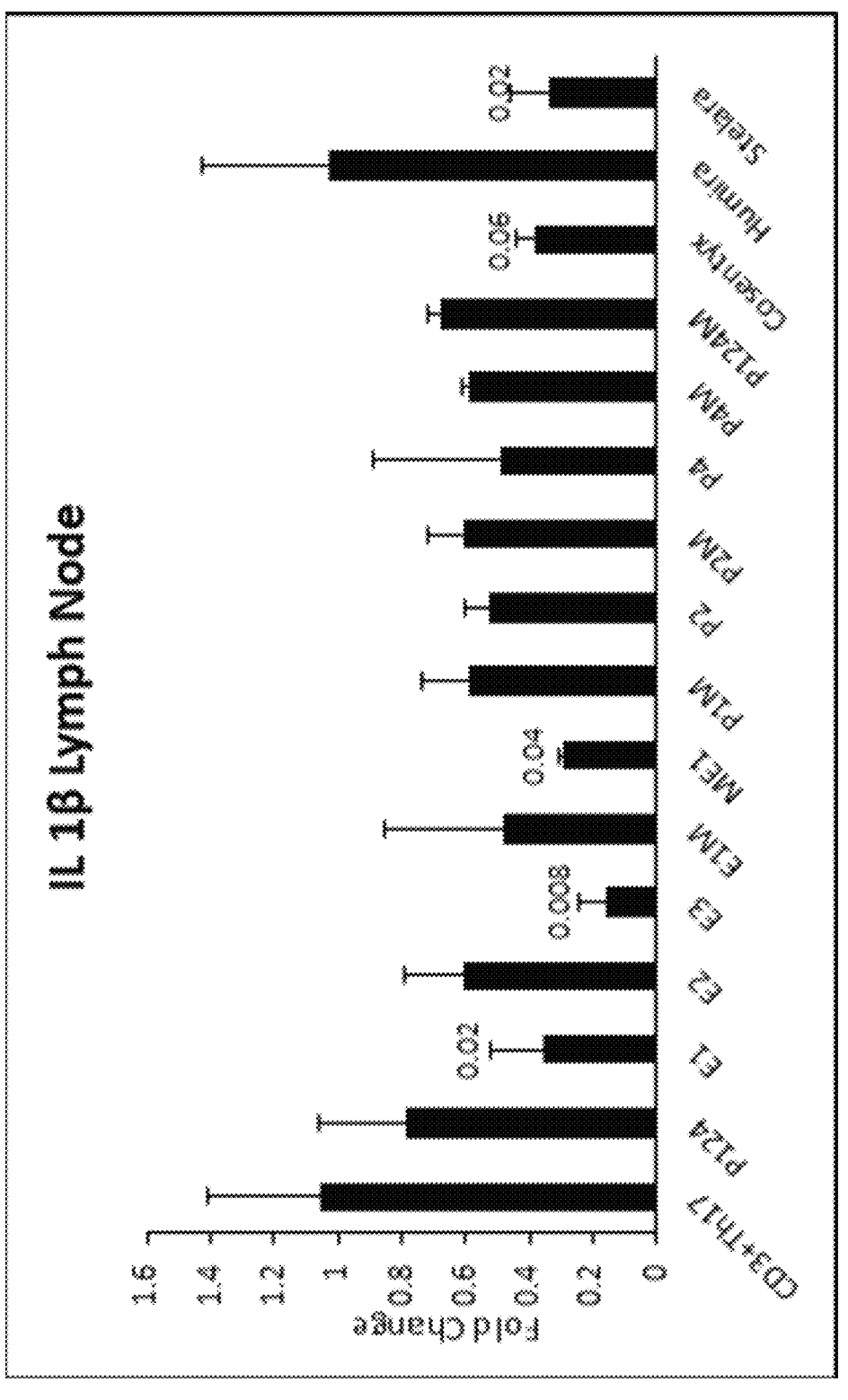
Figure 2I:
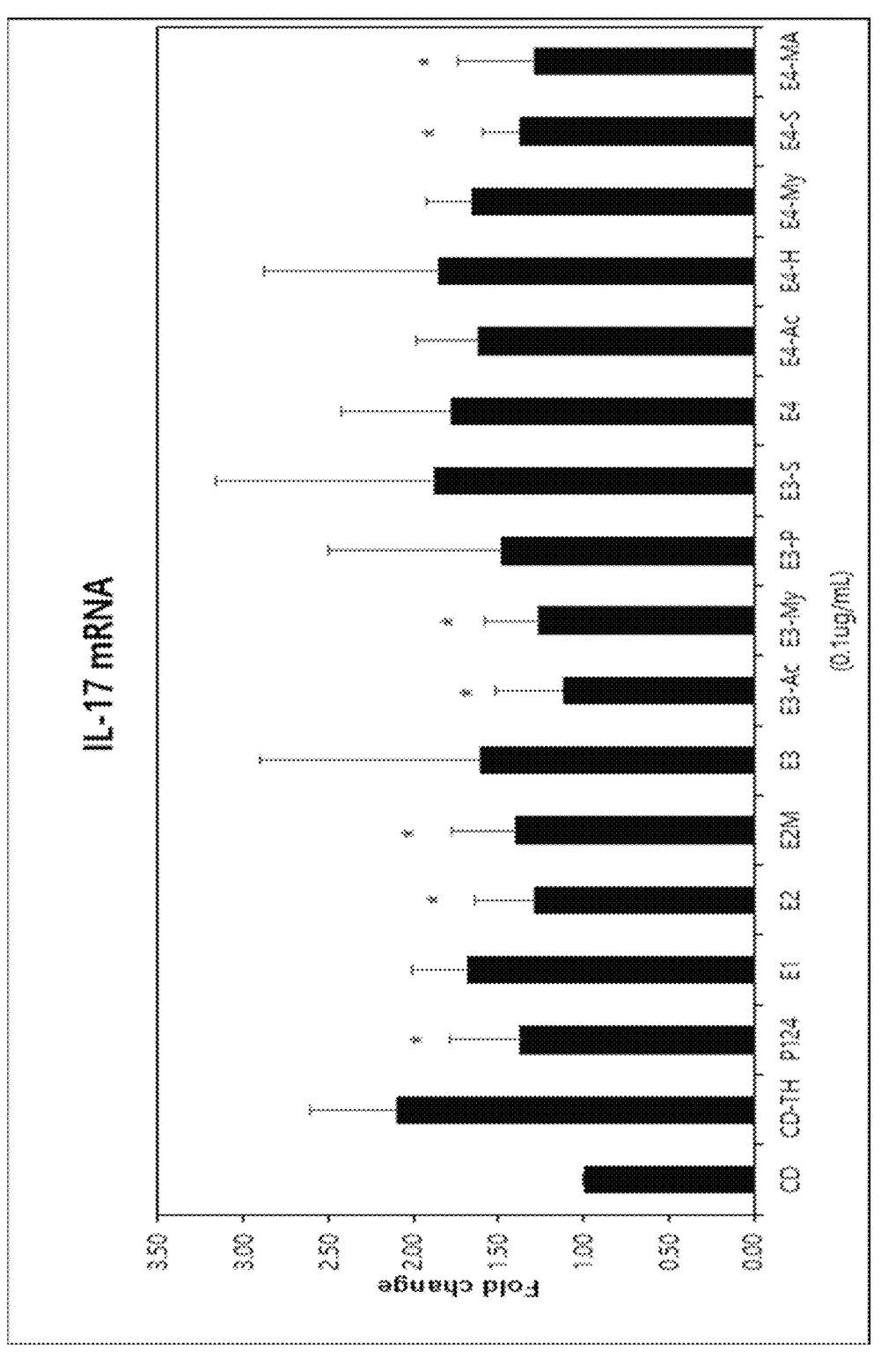
Figures 3A, 3B:
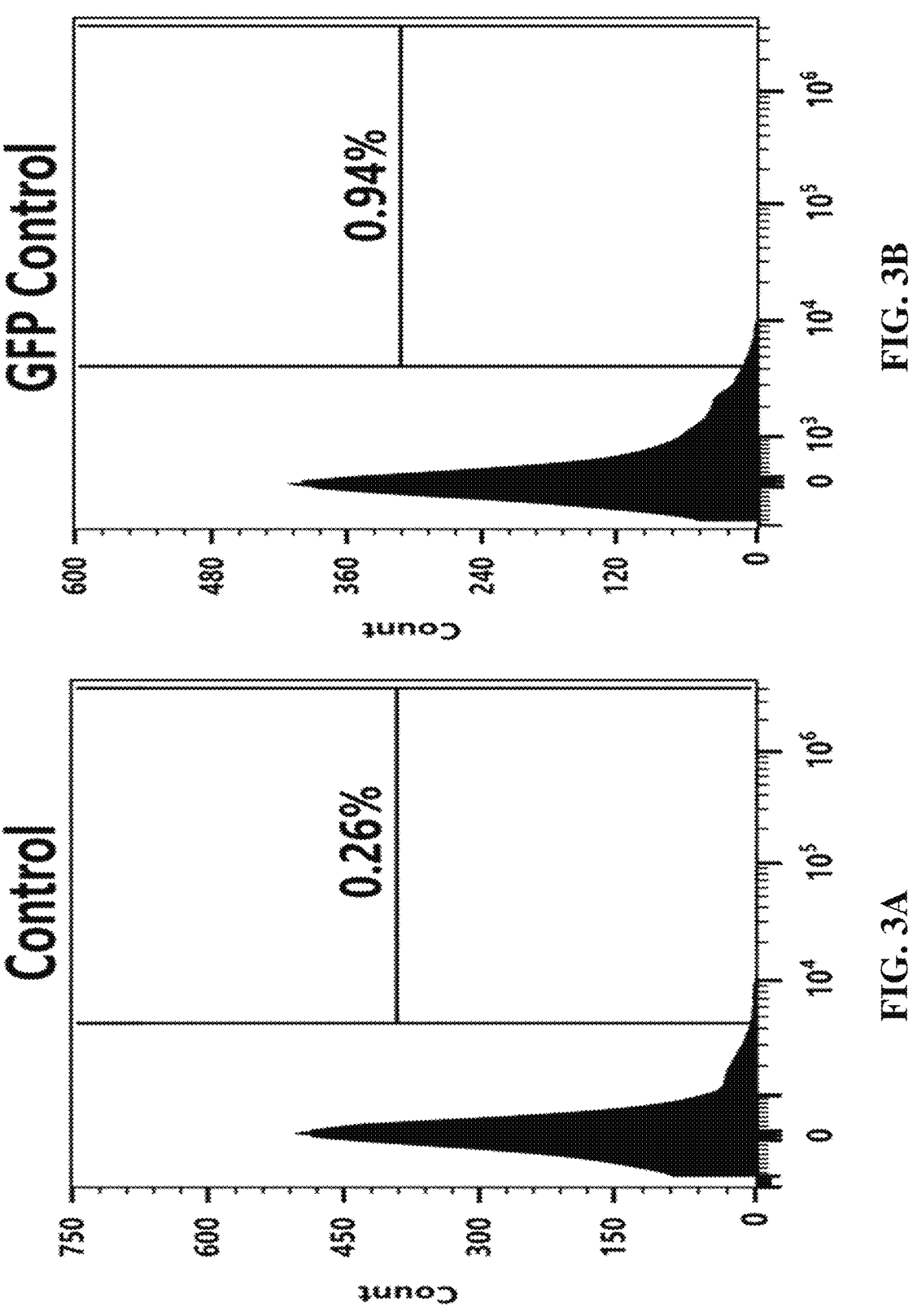
FIGS. 3A-3L show flow cytometry in cultures of peritoneal macrophages and lymph node cells.
Figures 3C, 3D:
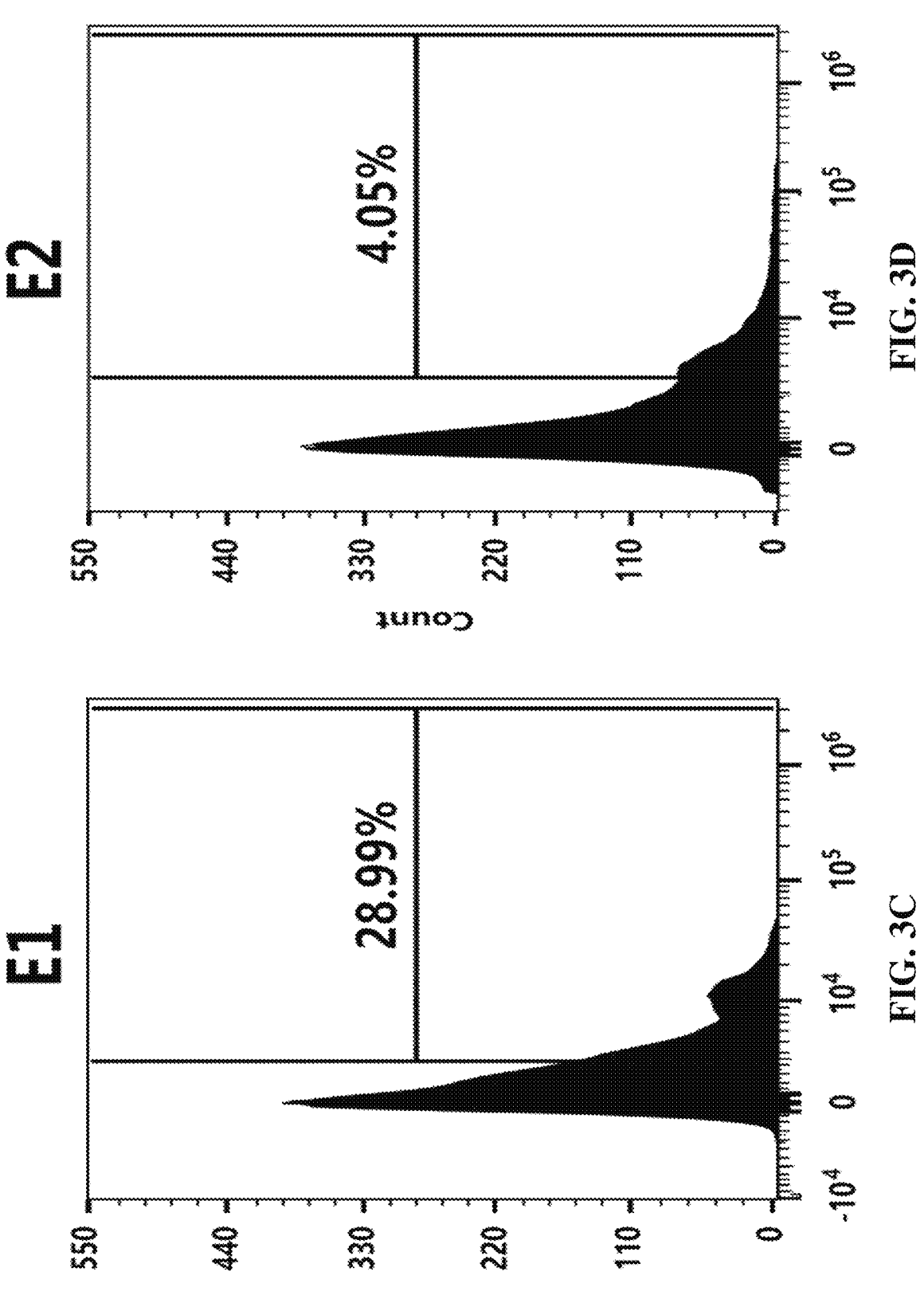
Figures 3E, 3F:
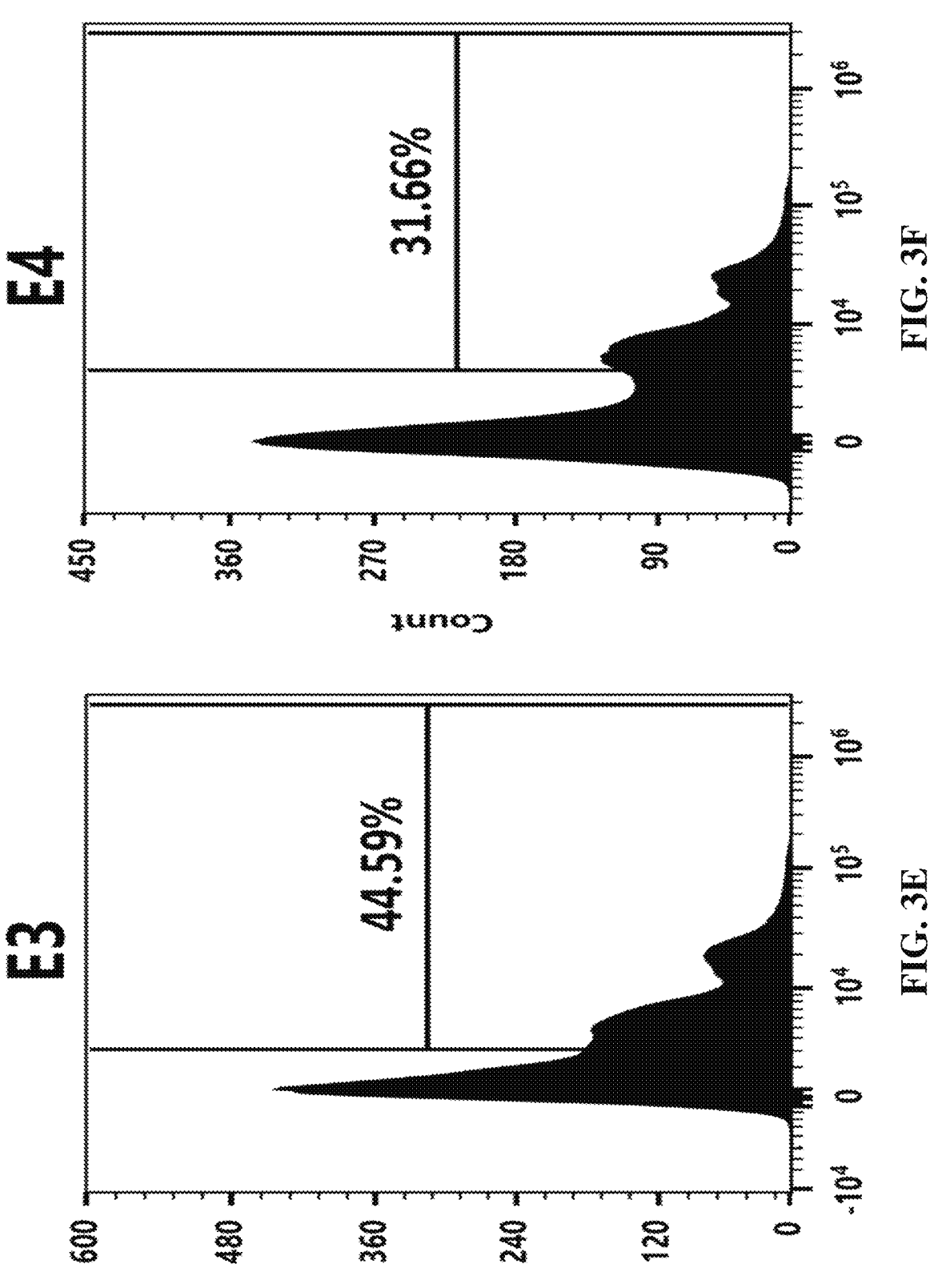
Figures 3G, 3H:
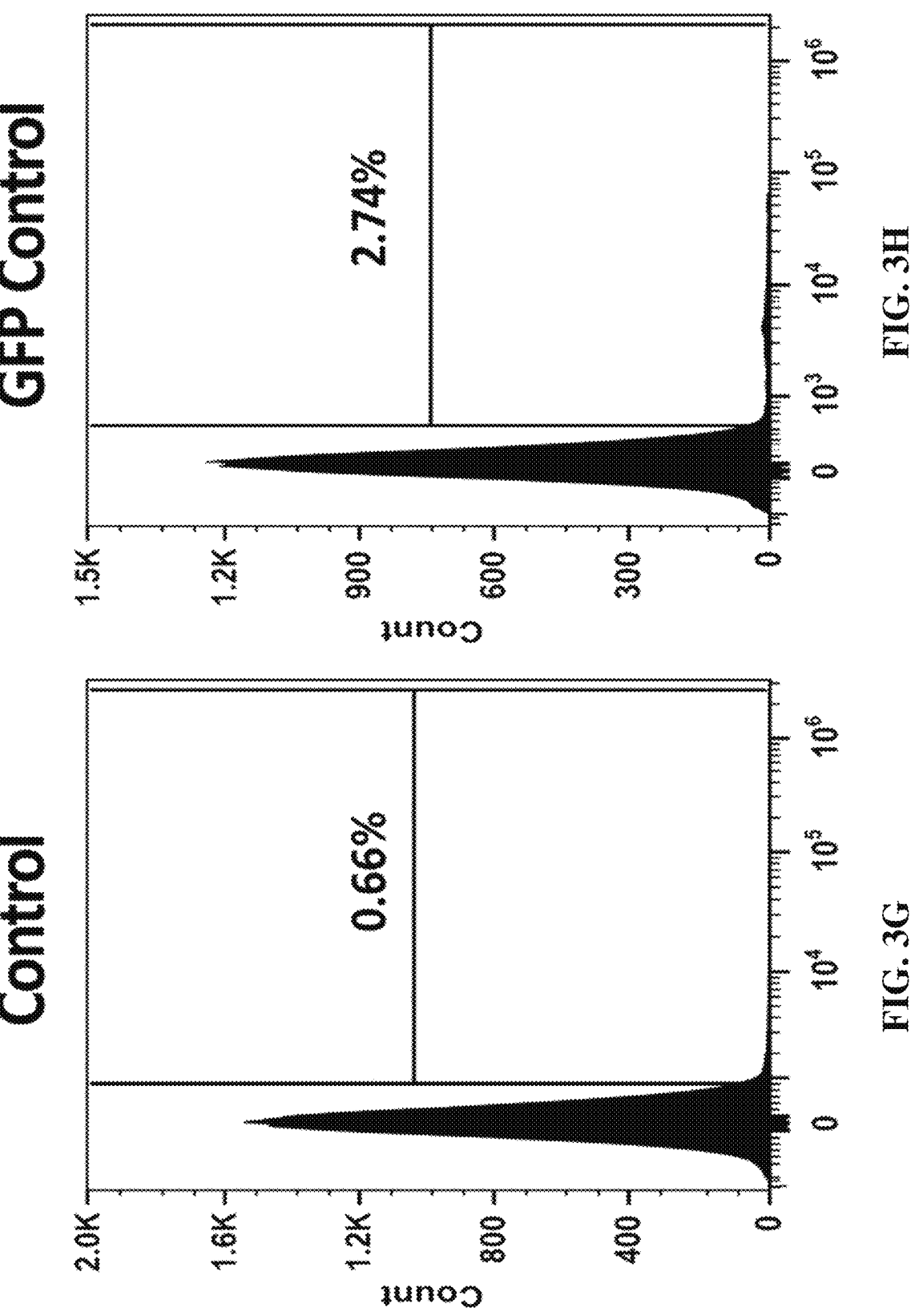
Figures 3I, 3J:
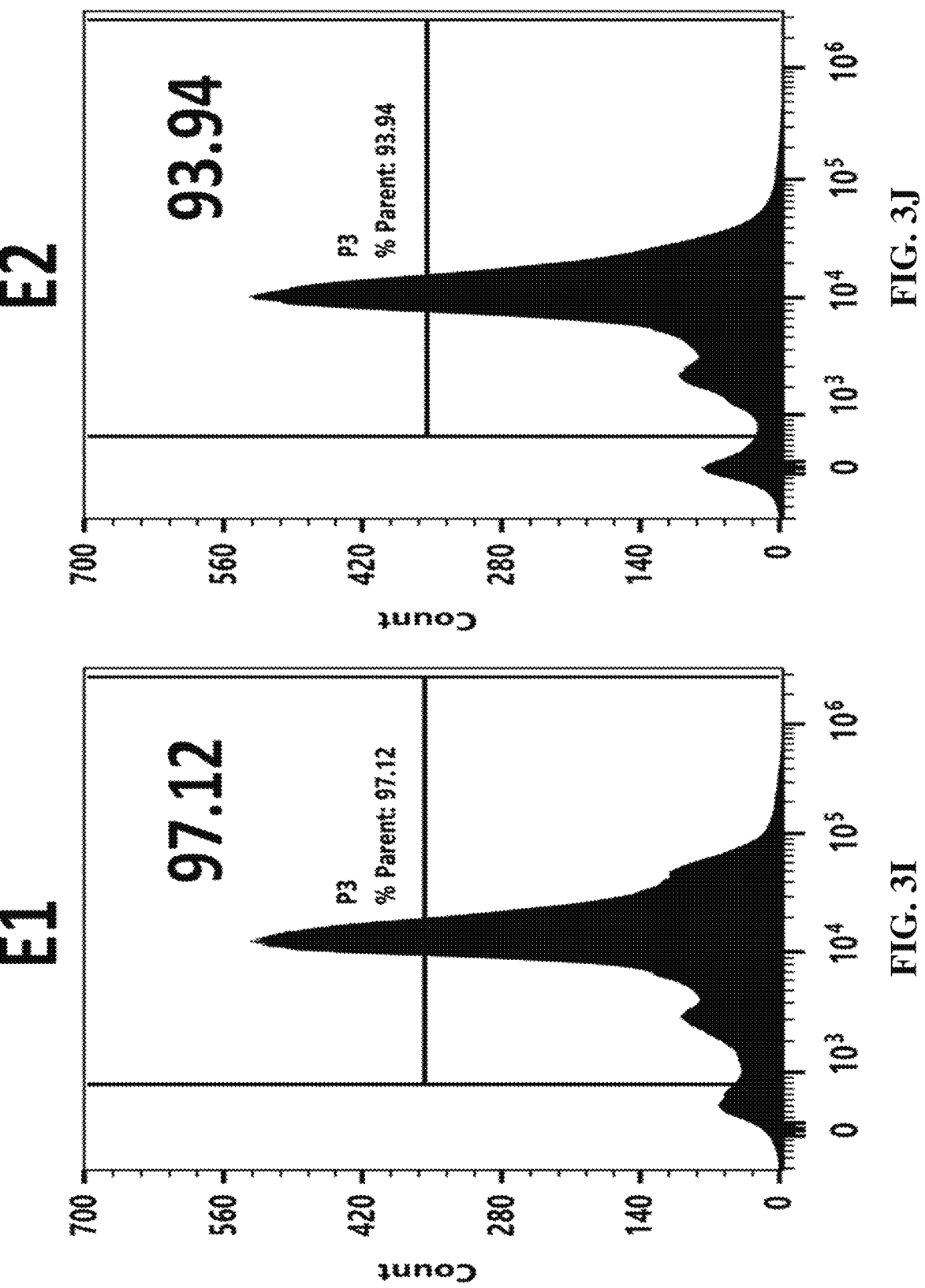
Figures 3K, 3L:
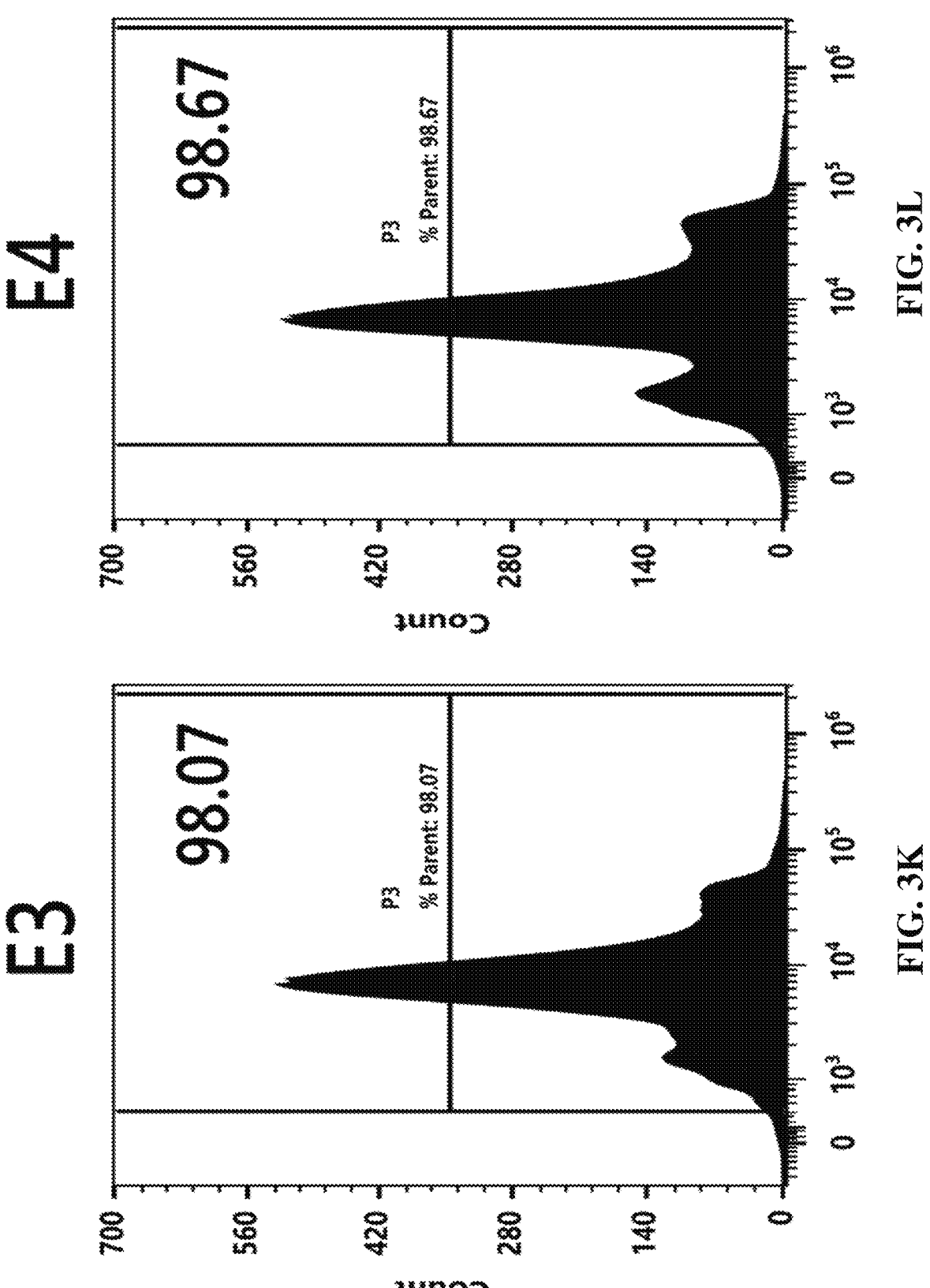
Figure 4:
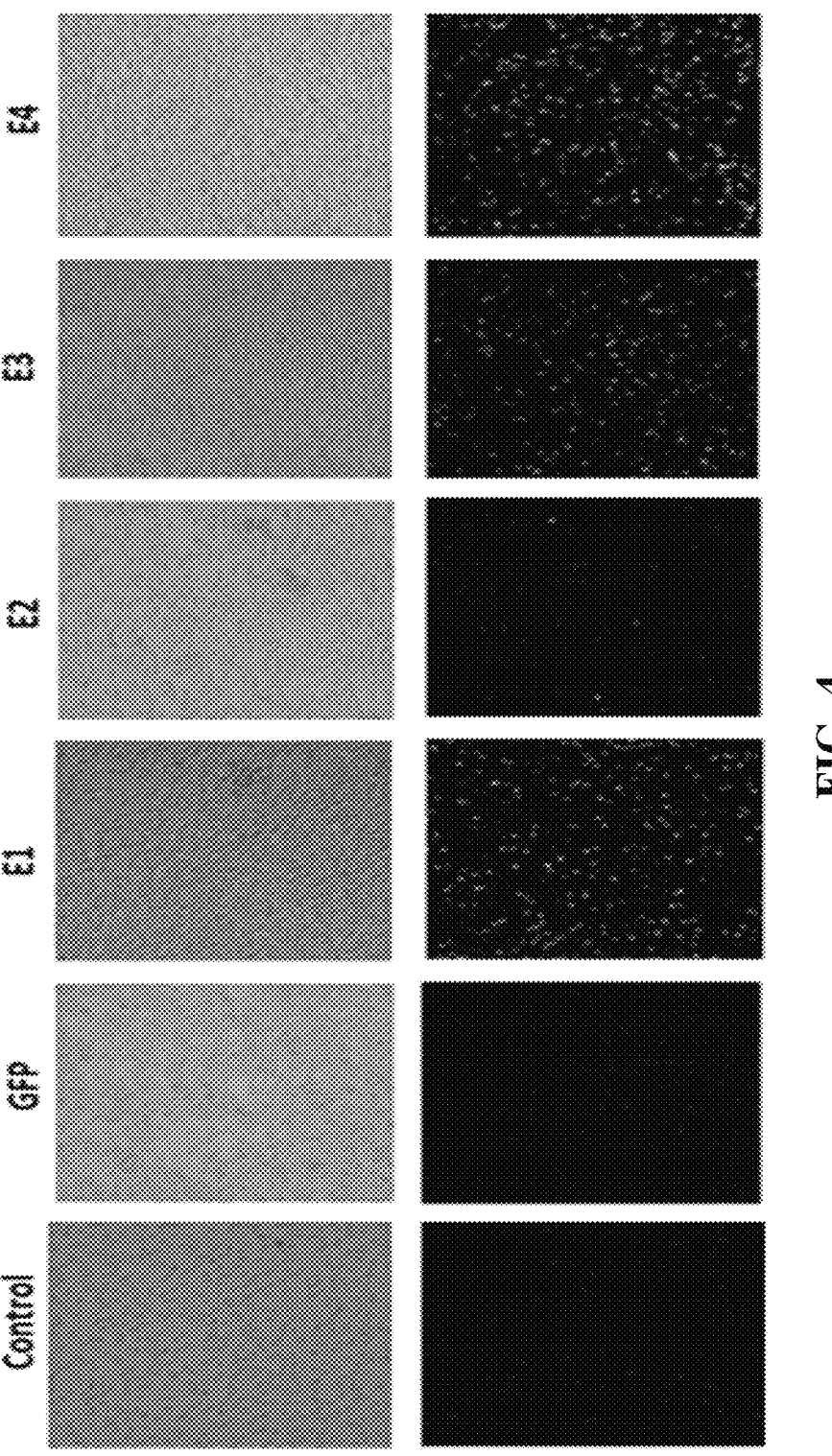
FIG. 4 shows an analysis under confocal microscope, conducted by administering FAM fluorescence-conjugated peptides into lymph node cell culture and then culturing the cell for 24 hours.

As a result, according to FIG. 2A, it was found that cytokine IL-17 was reduced by E1, E2, E3, and P2M in the spleen, according to FIG. 2B, expression of ROR-gammaT gene in the spleen was reduced by E3, according to FIG. 2C, cytokine TNF-alpha in the spleen was reduced by E1, E2, E3, P2M, P4M, and P124M, according to FIG. 2D, cytokine IL-1 beta in the spleen was reduced by E1, E2, E3, E1M, P1M, P4M, and P124M, according to FIG. 2E, cytokine IL-17 in the lymph node was reduced by E1, E2, E3, E1M, P2M, and P4M, according to FIG. 2F, expression of ROR-gammaT gene in the lymph node was reduced by E1, E2, E3, and E1M, according to FIG. 2G, cytokine TNF-alpha in the lymph node was reduced by E2, E3, E1M, and ME1, according to FIG. 2H, cytokine IL-1 beta in the lymph node was reduced by E1, E3, and ME1, and according to FIG. 2I, cytokine IL-17 in spleen mRNA was significantly reduced by E2M, E3-Ac, E3-My, E4-S, and E4-MA (*: P<0.05).

[Experimental Example 3] Flow Cytometry in Cultures of Peritoneal Macrophages and Lymph Node Cells In Vitro Flow cytometry was conducted in the cultures of peritoneal macrophages and lymph node cells in vitro. Lymph node cells were cultured at $0.5 \times 10^6$ cells/mL in a well plate. After 24 hours, cells were washed twice with PBS and cultured with peptides in serum-containing DMEM at 37° C. for 1 hour. On the other hand, peritoneal macrophages were cultured at $2 \times 10^5$ cells/mL. After 24 hours, cells were washed twice with PBS and cultured with peptides in serum-containing DMEM at 37° C. for 1 hour. Thereafter, E1 to E4 were treated by 1 µg/mL each in abdominal macrophages and lymph node cells, followed by observation after 24 hours of culture. For the flow cytometry, peptides labeled with FAM, a fluorescent substance, were treated to the culture medium of cells being cultured, and after 24 hours of culture, the frequency of fluorescently labeled cells was measured among the entire cells in the flow cytometer, resulting in detection of the peptide having entered the cell. The analysis was performed using a Cytek Aurora flow cytometry instrument.

As a result, according to FIG. 3A to FIG. 3L, when treating each peptide while culturing abdominal macrophages and lymph node cells, it was found that the peptide entered the cultured cells.

[Experimental Example 4] Observation Under Fluorescence Microscope after Peptide Treatment to Lymph Node Cells Lymph node cell cultures were treated with E1 to E4 peptides by 1 µg/mL each, and after 24 hours, phase contrast images and fluorescence microscope were used to check whether peptides labeled with FAM, the fluorescent substance, had entered the cells. The Zeiss LSM980 model was used as the confocal fluorescence microscope.

As a result, according to FIGS. 3A-3L, when the FAM labeled peptide was treated while culturing the lymph node cells, it was detected that cells were fluorescently labeled as the peptides entered the cultured lymph node cells.

[Experimental Example 5] Observation Under Fluorescence Microscope after Peptide Treatment onto Mouse Skin Observed with fluorescence microscope were tissue sections obtained 2 hours after applying a peptide-including external agent to mouse skin and tissue sections obtained 2 hours after applying a peptide-including external agent after making scratches on the mouse skin. A solution mixed with 1 µg of E1 to E4 peptides and 100 µL of distilled water was used as an external agent to be applied to the skin using a cotton swab.

Figure 5A:
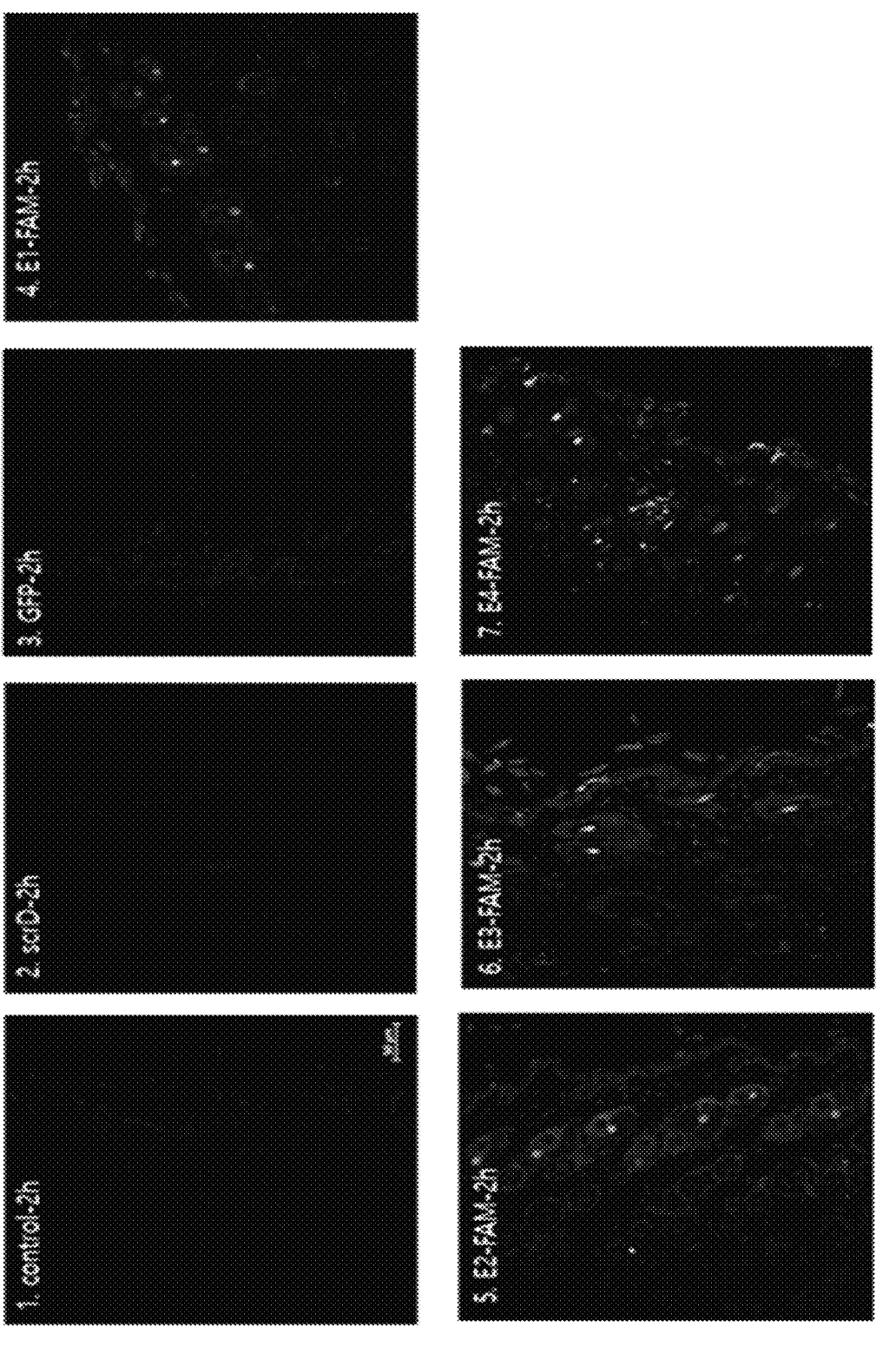
FIGS. 5A-5B show results of identifying, under fluorescence microscope, tissue fragments obtained 2 hours after applying peptides to a mouse skin.
Figure 5B:
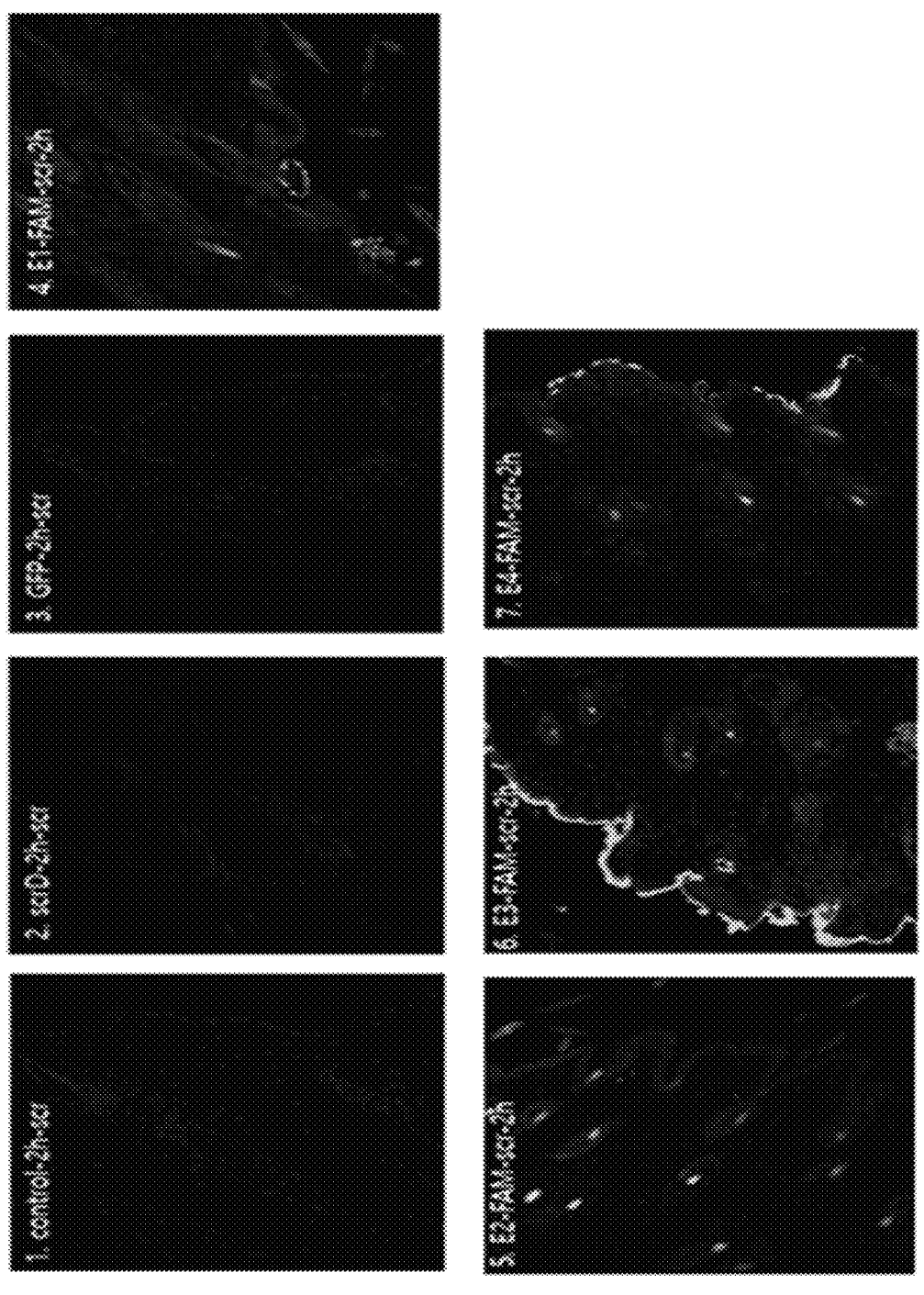

As a result, according to FIGS. 5A and 5B, when the peptides were applied to the skin, it was found that the peptides penetrated the lower part of the epidermis of any mouse with or without wounds on the skin.

Experimental Example 6] Determination of Skin Symptom Improvement in Mice with Behçet's Disease After applying the peptide-including external agent used in the Experimental Example 5 to the skin of mice with Behçet's disease, changes in the symptom improvement were checked. Administration was performed by 1 µg/mouse once a day for 10 days.

Figure 6:
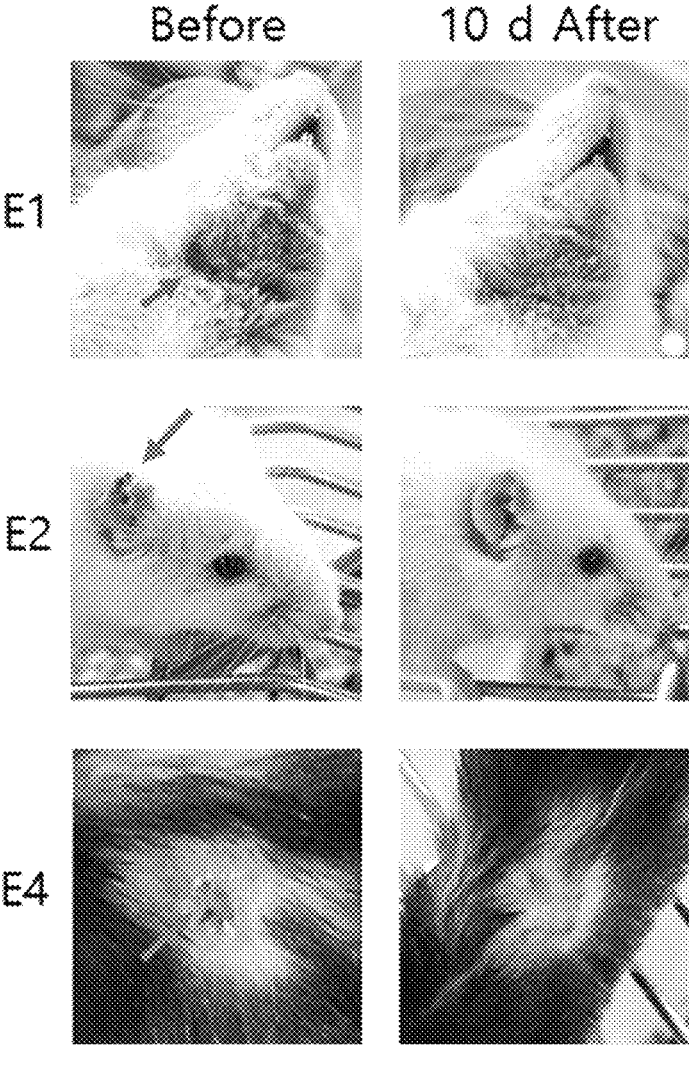
FIG. 6 shows changes in symptom improvement after applying peptides to the skin of mice with Behçet's disease.
Figure 7A:
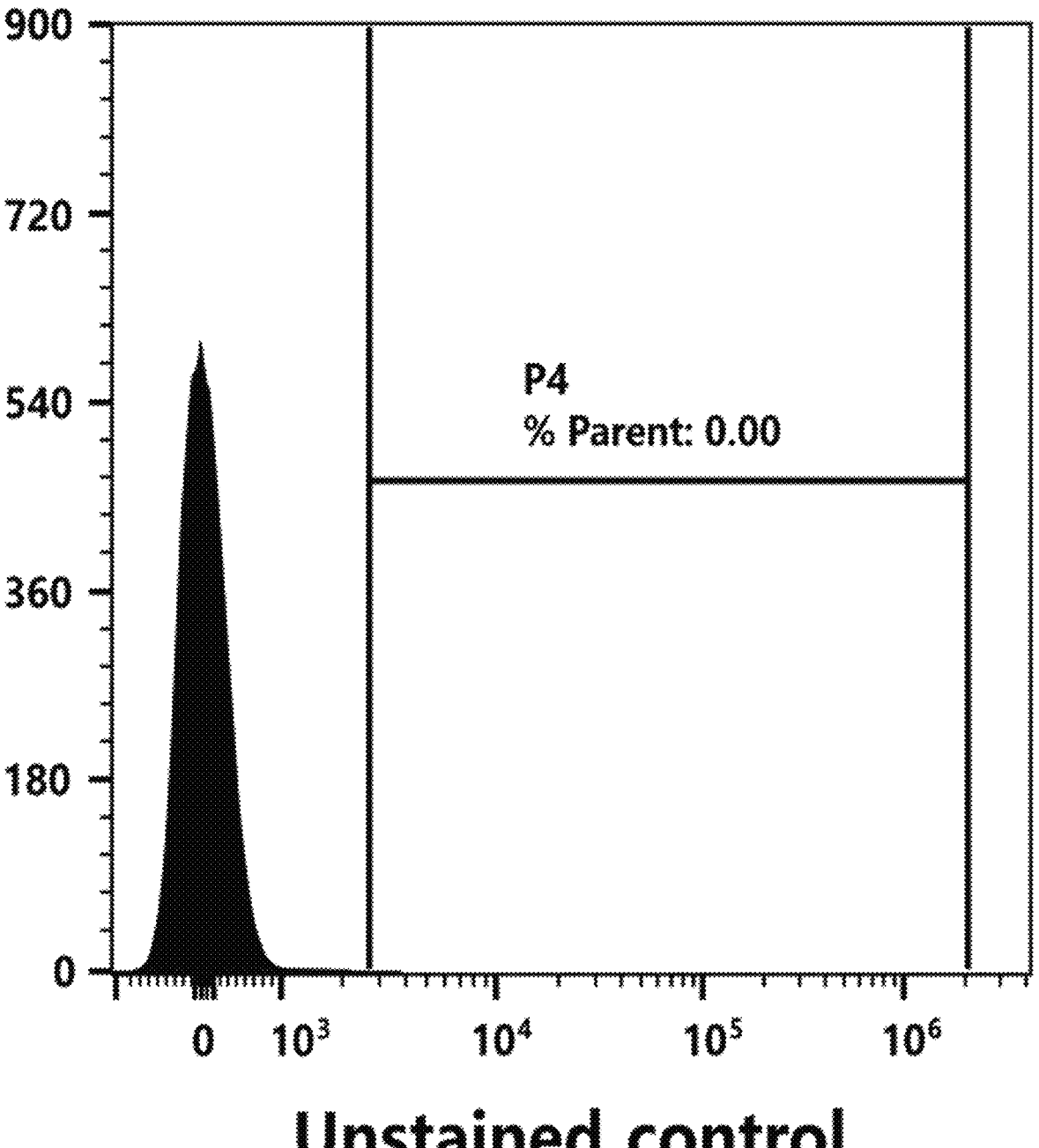
FIGS. 7A-7D show a comparative analysis on a frequency of CD83-labeled cells, which are dendritic cell activation markers, via a flow cytometer after administering peptides into mice with Behçet's disease.
Figure 7B:
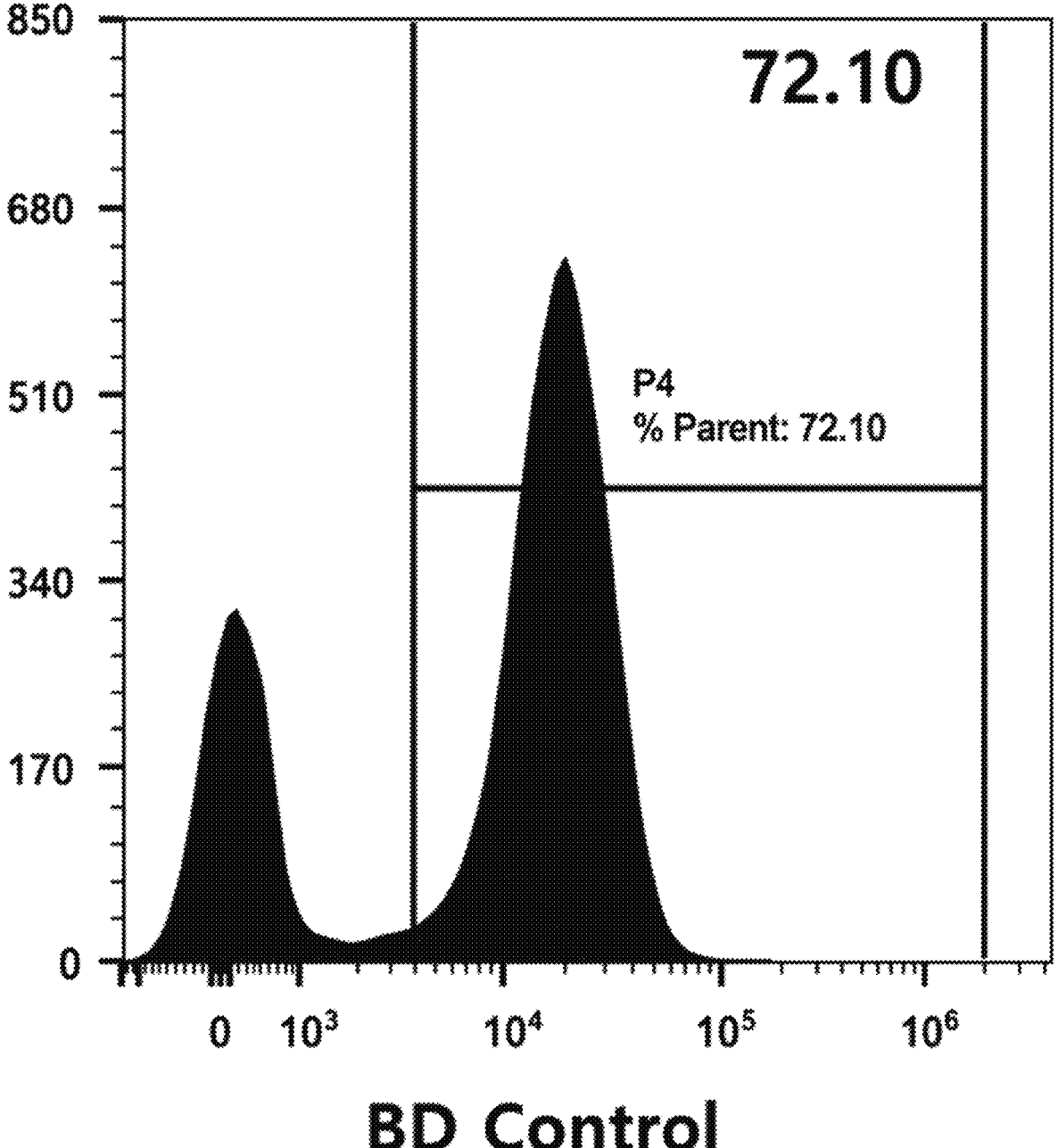
Figure 7C:
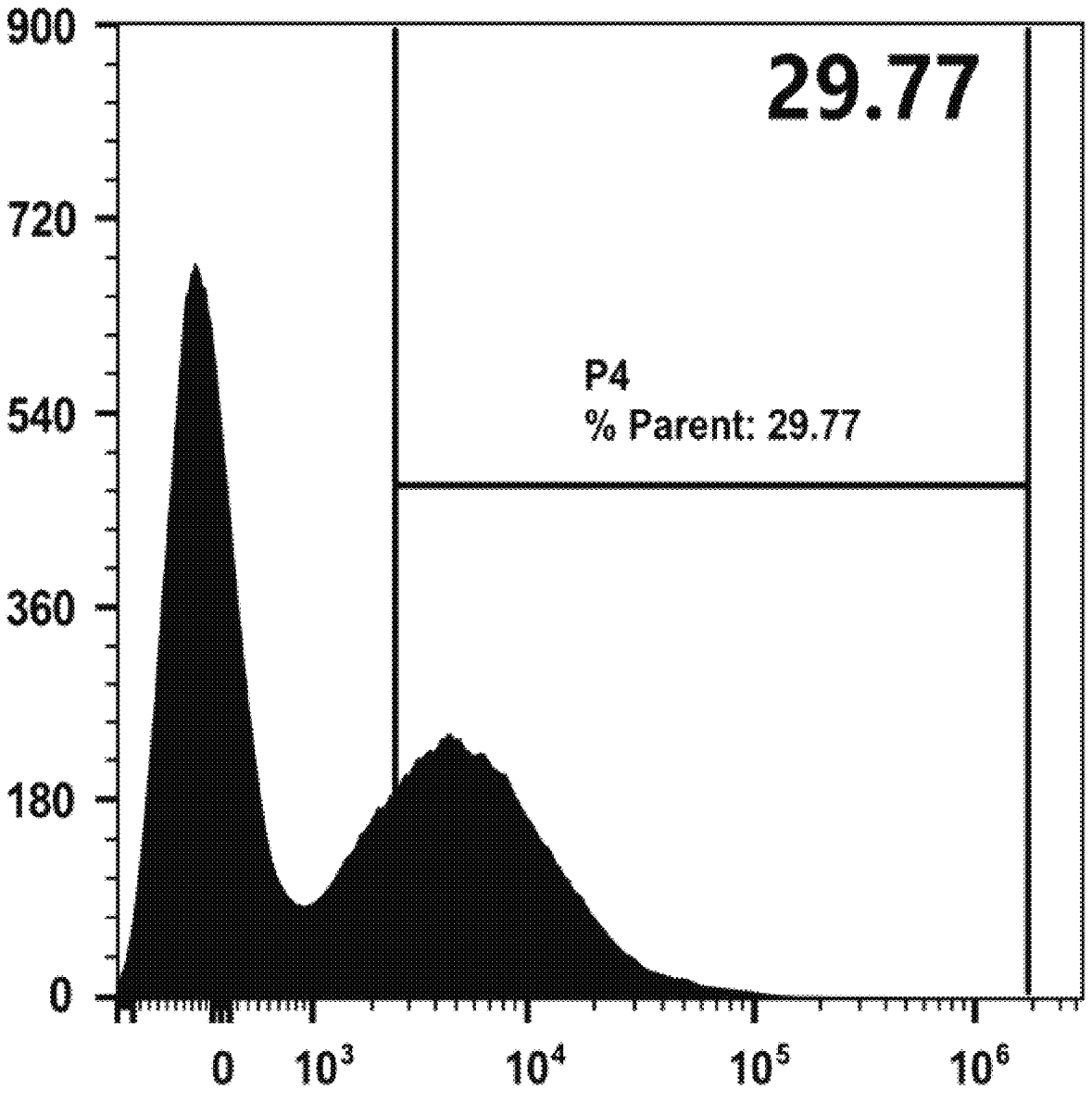
Figure 7D:
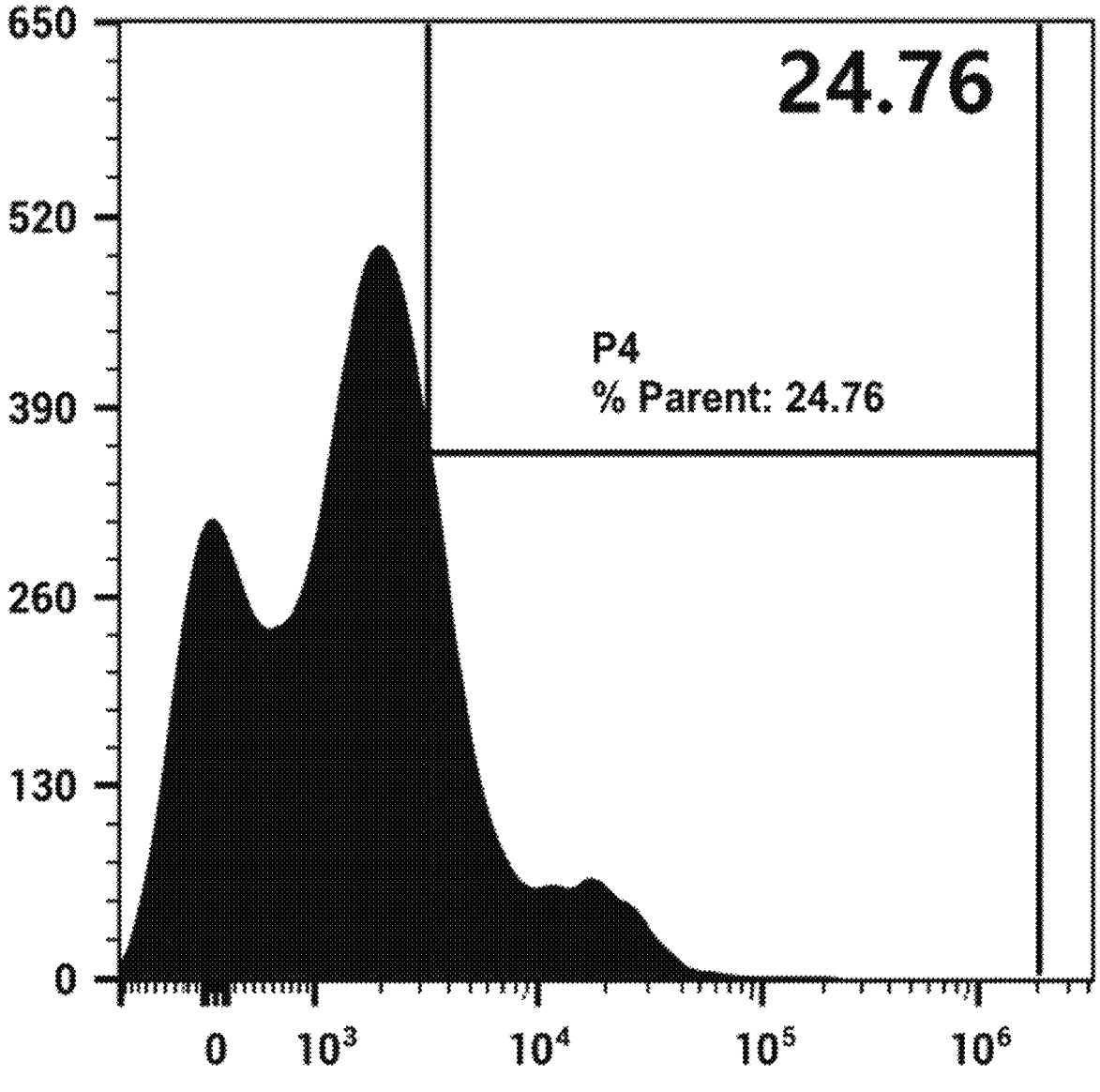

As a result, according to FIG. 6, it was found that: the ulcer under the jaw improved after administration of the external agent, in which E1 was used, to the skin ulcer of mice with Behçet's diseases, and the symptom almost disappeared after 10 days; the external agent in which E2 was used and which was administered to tissue necrosis and cutaneous erythema in the auricle improved the skin erythema; and the external agent in which E4 was used made skin ulcer that was developed on the back of C57BL/6 mice as one of the symptoms of Behçet's disease almost disappeared after 10 days, and the wound healed.

[Experimental Example 7] Identification of a Frequency of CD83-Labeled Cells, a Dendritic Cell Activation Marker, after Administration of Peptides to Mice with Behçet's Disease After administering P124 and P124M peptides to mice with Behçet's disease, the frequency of CD83-labeled cells, which are dendritic cell activation markers, was checked. After administering peptides to mice with Behçet's disease, blood cells were isolated from peripheral blood cells and stained with fluorescently labeled anti-CD83 antibodies, and the frequency of fluorescently labeled cells was analyzed by flow cytometry.

As a result, according to FIGS. 7A-7D, it was found that the frequency of CD83 expressing cells among the blood cells in the blood of mice with Behçet's disease whose symptoms were improved by P124 peptide administration was reduced, and P124M peptide administration reduced the frequency of CD83 expressing cells in mice with Behçet's disease than the P124 administered mice.

[Experimental Example 8] Analysis of a Frequency of Ly6G+ (Neutrophil) Cells in Peripheral Blood Cells after Administering Peptides to Arthritis Model Mouse (Collagen Induced Arthritis, CIA)

Collagen was mixed with an adjuvant and injected subcutaneously into the tail twice (Day 1 and Day 11) to prepare arthritis model mice. The adjuvant is a mixture of 17 μL of high-concentration paraffin oil (Fisher, cat. no. 0122-1) and 68 μg (17 μL) of complete Freund adjuvant (CFA; Sigma-Aldrich, cat. no. F5881), which was used by mixing with 34 μg (17 μL) of bovine type II collagen (MD bioproducts cat. no. 804001-Sol). From the day after the second collagen injection (day 12), 1 μg (100 μL) of peptide was administered intramuscularly to the hind legs 10 times (once every 2 days), and mouse peripheral blood cells were isolated to analyze the frequency of Ly6G+ cells via flow cytometry. Peripheral blood cells were isolated from mouse hearts, red blood cells were lysed in ACK buffer (ammonium-chloride-potassium lysing buffer), and then centrifugation was performed to collect only blood cells to be used for antibody staining for the analysis with the flow cytometer. Using Ly6G+ as a neutrophil marker, whether the peptide inhibits a frequency of inflammation-induced neutrophil cells in an arthritis model was determined. Methotrexate (MTX) was used as a control drug.

Figure 8:
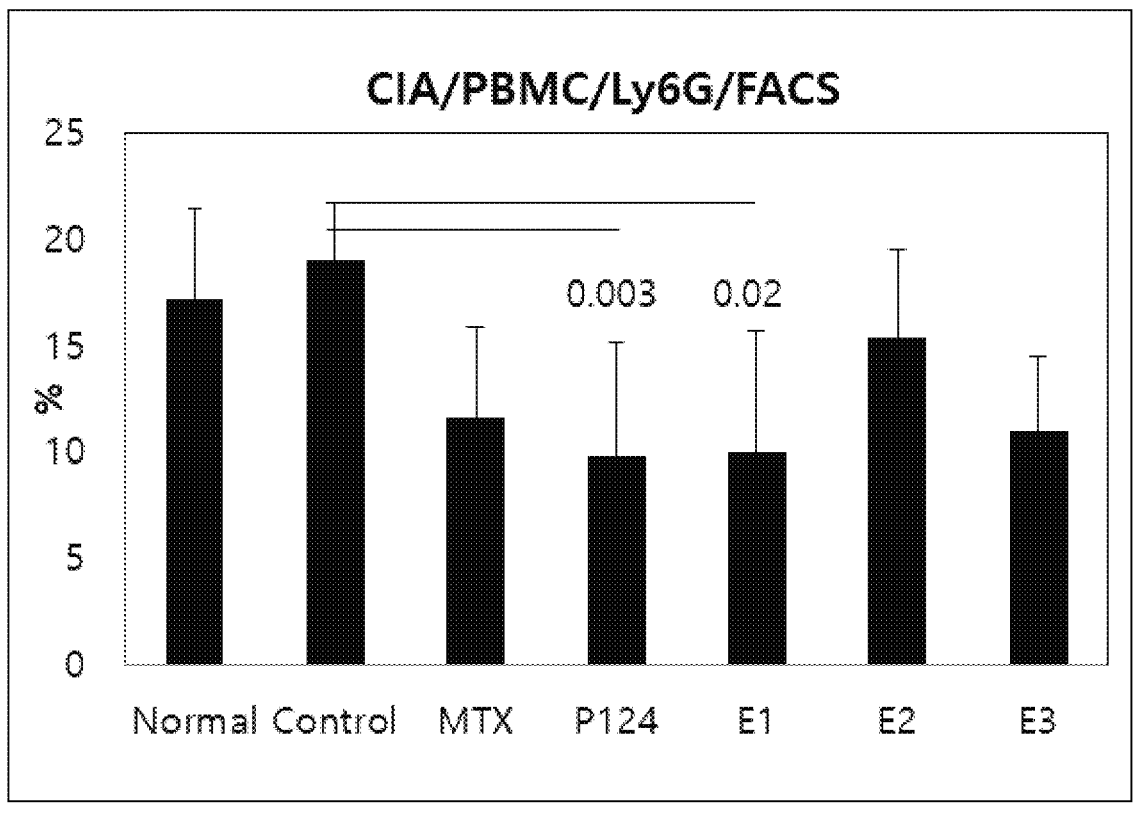
FIG. 8 shows an analysis on a frequency of Ly6G+ (neutrophils) cells via flow cytometer in peripheral blood cells after administering peptides into arthritis model mice (collagen induced arthritis, CIA).

As a result, according to FIG. 8, it was found that the frequency of Ly6G+ cells decreased to a statistically significant level in the P124 and E1 peptide treated groups.

[Experimental Example 9] Changes in an Ankle Thickness after Peptide Administration to Arthritis Model Mice (Collagen Induced Arthritis, CIA)

Since the thickness of the ankle increases due to edema caused by arthritis, the ankle thickness was measured to determine whether peptide administration may relieve edema caused by inflammation. The ankle thickness was measured with a digital caliper at the thickest part of the ankle.

Figure 9A:
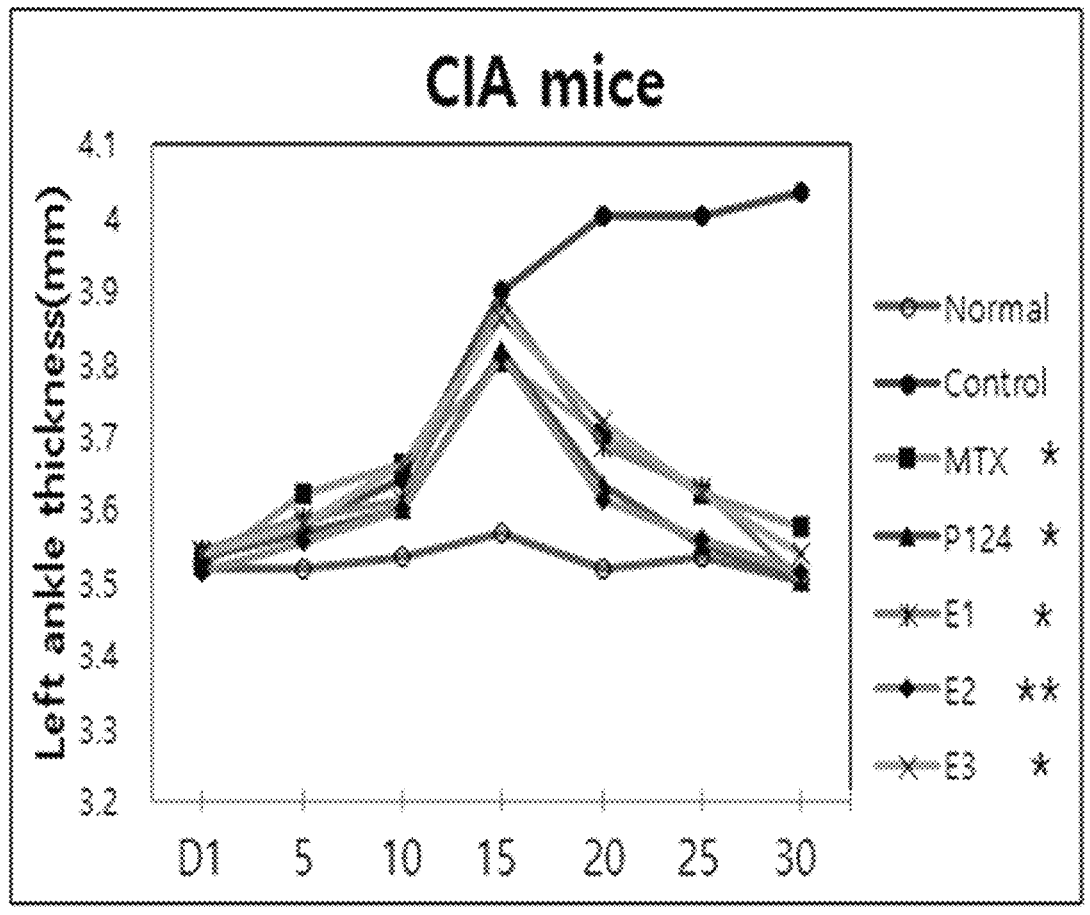
FIGS. 9A-9B show changes in an ankle thickness after administering peptides into arthritis model mice (collagen induced arthritis, CIA).
Figure 9B:
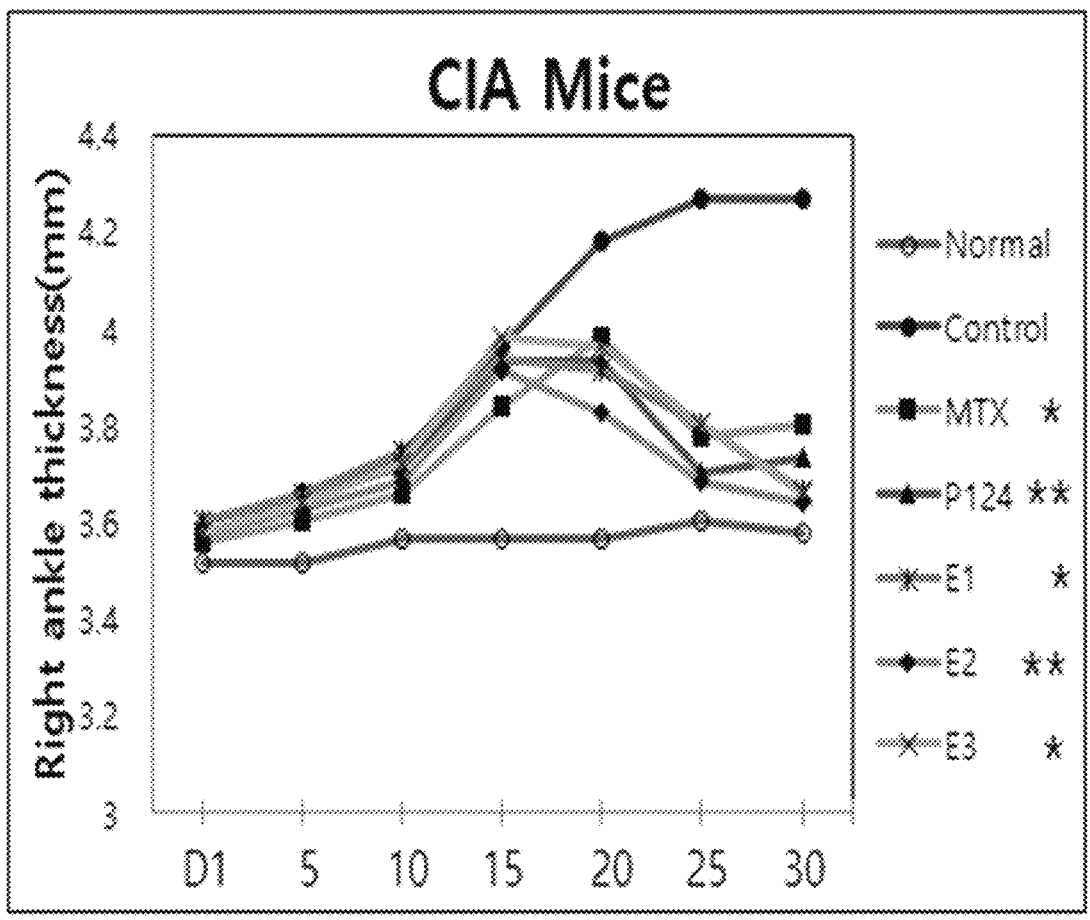

As a result, according to FIGS. 9A-9B, it was found that the thickness of the ankle was significantly reduced at day 30 compared to arthritis mice (control) without receiving peptides in the P124, E1, E2, and E3 peptide administered groups.

The foregoing description of the present disclosure is for illustrative purposes only, and a person of ordinary skill in the art to which the present disclosure pertains will be able to understand that it may be easily modified into other concrete forms without changing the technical idea or essential features of the present disclosure. Therefore, the example embodiments described above should be understood as exemplary and not limited in all respects.

The scope of the present disclosure is indicated by the claims described below, and the meaning and scope of the claims and all altered or modified forms derived from the concept of equivalence thereof should be construed as being included in the scope of the present disclosure.

The invention claimed is:

1. A peptide comprising an amino acid sequence selected from the group consisting of SEQ ID NOs: 1, 2, 3, 4, 5, 6, and 7.

2. The peptide of claim 1, wherein the N- or C-terminus comprises a palmitoyl group, a hexanoyl group, a myristoyl group, a stearoyl group, an acetyl group, a maleimidobutyryl group, or a PEG.

3. A conjugate comprising the peptide according to claim 1 conjugated to a biocompatible polymer or fatty acid.

4. The conjugate of claim 3, wherein the biocompatible polymer is one or two or more selected from the group consisting of pullulan, chondroitin sulfate, hyaluronic acid (HA), glycol chitosan, starch, chitosan, dextran, pectin, curdlan, poly-L-lysine, poly-aspartic acid (PAA), polylactic acid (PLA), polyglycolide (PGA), poly(ε-caprolactone) (PCL), poly(caprolactone-lactide) random copolymer (PCLA), poly(caprolactone-glycolide) random copolymer (PCGA), poly(lactide-glycolide) random copolymer (PCGA), polyethylene glycol (PEG), pluronic F-68, and pluronic F-127.

5. The conjugate of claim 3, wherein the fatty acid is one or two or more selected from the group consisting of hexanoic acid, caprylic acid, capric acid, maleimidobutyric acid, lauric acid, myristic acid, palmitic acid, stearic acid, and cholesterol.

6. A pharmaceutical composition for treating or preventing an inflammatory disease or autoimmune disease, comprising one or more peptide(s) selected from the group consisting of the peptide(s) according to claim 1.

7. The pharmaceutical composition of claim 6, wherein the pharmaceutical composition is any one selected from the group consisting of an oral agent, external agent, suppository, and injection agent.

8. A cosmetic composition for preventing or alleviating an inflammatory disease or autoimmune disease, comprising one or more peptide(s) selected from the group consisting of the peptide(s) according to claim 1.

9. The cosmetic composition of claim 8, wherein the cosmetic composition has a formulation of a softening toner, nourishing toner, nourishing cream, gel, essence, soap, ointment, balm, or pack.

10. A health functional food composition for preventing or alleviating an inflammatory disease or autoimmune disease, comprising one or more peptide(s) selected from the group consisting of the peptide(s) according to claim 1.

11. A pharmaceutical composition for treating or preventing an inflammatory disease or autoimmune disease, comprising one or more conjugate(s) selected from the group consisting of the conjugates(s) according to claim 3 as an active ingredient.

12. A cosmetic composition for preventing or alleviating an inflammatory disease or autoimmune disease, comprising one or more conjugate(s) selected from the group consisting of the conjugate(s) according to claim 3 as an active ingredient.

13. A health functional food composition for preventing or alleviating an inflammatory disease or autoimmune disease, comprising one or more conjugate(s) selected from the group consisting of the conjugate(s) according to claim 3 as an active ingredient.

* * * * *